(12) United States Patent
De Vreese et al.

(10) Patent No.: US 9,993,459 B2
(45) Date of Patent: Jun. 12, 2018

(54) SELECTIVE HDAC6 INHIBITORS AND USES THEREOF

(71) Applicant: Universiteit Gent, Ghent (BE)

(72) Inventors: Rob De Vreese, Wevelgem (BE); Matthias D'Hooghe, Evergem (BE)

(73) Assignee: Universiteit Gent, Ghent (BE)

( * ) Notice: Subject to any disclaimer, the term of this patent is extended or adjusted under 35 U.S.C. 154(b) by 0 days. days.

(21) Appl. No.: 15/540,316

(22) PCT Filed: Jan. 7, 2016

(86) PCT No.: PCT/EP2016/050217
§ 371 (c)(1),
(2) Date: Jun. 28, 2017

(87) PCT Pub. No.: WO2016/110541
PCT Pub. Date: Jul. 14, 2016

(65) Prior Publication Data
US 2017/0360748 A1    Dec. 21, 2017

(30) Foreign Application Priority Data
Jan. 8, 2015 (EP) ................................. 15150446

(51) Int. Cl.
| | | |
|---|---|---|
| A61K 31/381 | (2006.01) | |
| C07D 333/58 | (2006.01) | |
| A61K 31/4045 | (2006.01) | |
| C07D 209/14 | (2006.01) | |
| A61K 45/06 | (2006.01) | |

(52) U.S. Cl.
CPC ........ *A61K 31/381* (2013.01); *A61K 31/4045* (2013.01); *C07D 209/14* (2013.01); *C07D 333/58* (2013.01); *A61K 45/06* (2013.01)

(58) Field of Classification Search
None
See application file for complete search history.

(56) References Cited

FOREIGN PATENT DOCUMENTS

| CN | 103467359 | * 12/2013 |
|---|---|---|
| CN | 103467359 A | 12/2013 |
| WO | WO2007109178 A2 | 9/2007 |
| WO | WO2011011186 A3 | 1/2011 |
| WO | WO2011106632 A1 | 9/2011 |
| WO | WO2012106343 A3 | 8/2012 |
| WO | WO2013134467 A1 | 9/2013 |
| WO | WO2014147178 A1 | 9/2014 |

OTHER PUBLICATIONS

Kaliszczak et al. British Journal of Cancer 108, 342-350 (2013), (Year: 2013).*

International Search Report and Written Opinion dated Mar. 1, 2016 for PCT/EP2016/050217 Filed Jan. 7, 2016. pp. 1-14.
Extended European Search Report dated Mar. 5, 2015 for Application No. 15150446.1 Filed Jan. 8, 2015. pp. 1-8.
International Search Report and Written Opinion dated May 22, 2014 for PCT/EP2014/055602 Filed Mar. 20, 2014. pp. 1-12.
"N-Hydroxy-3-phenyl-2-propenamides as Novel Inhibitors of Human Histone Deacetylase with in Vivo Antitumor Activity: Discovery of (2E)-N Hydroxy-3[4-[[(2-hydroxyethyl)[2-(H-indol-3-yl)ethyl]amino]methyl]-phyenl]-2-propenamide (NVP-LAQ824)", Remiszewski, et al., J. Med. Chem 2003, pp. 4609-4624.
"A novel small molecule hydroxamate preferentially inhibits HDAC6 activity and tumor growth", Kaliszczak et al., British Journal of Cancer, 2013, pp. 345-350.
"Potent and Selective Inhibition of Histone Deacetylase 6 (HDAC6) Does Not Require a Surface-Binding Motif", Wagner, et al., Journal of Medicinal Chemistry, 2013, pp. 1772-1776.
"Rational Design and Simple Chemistry Yield a Superior, Neuroprotective HDAC6 Inhibitor, Tubastatin A", Butler, et al., J. Am Chem Soc., Jul. 9, 2010, pp. 10842-10846.
"Potent and selective HDAC6 inhibitory activity of N-(4-hydroxycarbamoylbenzyl)-1,2,4,9-tetrahydro-3-thiA-9-azafluorenes as novel sulfur analogues of Tubastatin A", DeVrees, et al., Chem. Comm. 2013, pp. 3775-3777.
"Development of a histone deacetylase 6 inhibitor and its biological effects", Lee et al., PNAS, 2013, pp. 15704-15709.
"Potent Histone Deacetylase Inhibitors Derived from 4-(Aminomethyl)-N-hydroxybenzamide with High Selectivity for the HDAC6 Isoform", Blackburn, et al., Journal of Medicinal Chemistry, 2013, pp. 7201-7211.

(Continued)

*Primary Examiner* — Dennis Heyer
(74) *Attorney, Agent, or Firm* — Dinsmore & Shohl LLP

(57) ABSTRACT

The present invention relates to selective Histone deacetylase 6 (HDAC6) inhibitors and compositions containing the same. Methods of treating diseases and conditions wherein inhibition of HDAC6 provides a benefit, like a cell proliferative disease, an autoimmune or inflammatory disorder, a neurodegenerative disease, or a combination thereof, also are disclosed.

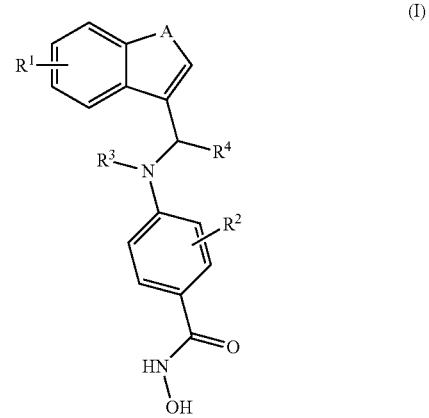

(I)

18 Claims, 5 Drawing Sheets

(56) References Cited

OTHER PUBLICATIONS

"Quinazolin-4-one Derivatives as Selective Histone Deacetylase-6 Inhibitors for the Treatment of Alzheimer's Disease", Yu, et al., Journal of Medicinal Chemistry, 2013, pp. 6775-6791.

"Novel HDAC6 isoform selective chiral small molecul histone deacetylase inhibitors", Smil, et al., Bioorganic & Medicinal Chemistry Letters, 2009, pp. 688-692.

"HDAC6 Regulates Hsp90 Acetylation and Chaperone-Dependent Activation of Glucocorticoid Receptor", Kovacs, et al., May 27, 2005, pp. 601-607.

"Synthesis and SAR assessment of novel Tubathian analogs in the pursuit of potent and selective HDAC6 inhibitors", De Vreese, et al, Organic & Biomolecular Chemistry, pp. 2537-2549.

"Synthesis of benzothiophene-based hydroxamic acids as potent and selective HDAC6 inhibitors", De Vreese, et al., 2015, pp. 9868-9871.

"Histone Deacetylase Inhibitors: Overview and Perspectives", Dokmanovic, et al., Mol. Cancer Research, 2007, pp. 981-989.

"Highly Potent and Selective Histone Deacetylase 6 Inhibitors Designed based on a Small-Molecular Substrate", Suzuki, et al., J. Med. Chem. 2006, pp. 4809-4812.

"Identification of Novel, Selective, and Stable Inhibitors of Class II Histone Deacetylases, Validation Studies of the Inhibition of the Enzymatic Activity of HDAC4 by Small Molecules as a Novel Approach for Cancer Therapy", Ontoria, et al., J. Med. Chem., 2009, pp. 6782-6789.

"Phenylalanine-containing hydroxamic acids as selective inhibitors of class IIb histone deacetylases (HDACs)", Schafer, et al., Bioorganic & Medicinal Chemistry, 2008, pp. 2011-2033.

"Pyridylalanine-Containing Hydroxamic Acids as Selective HDAC6 Inhibitors", Schafer, et al., Chem. Med. Chem., 2009, pp. 283-290.

"Inhibitors selective HDAC6 in enzymes and cells", Gupta, et al., Bioorganic & Medicinal Chemistry Letters, 2010, pp. 7067-7070.

"HDAC6 is a target for protection and regeneration following injury in the nervous system", Rivieccio, et al., PNAS, Nov. 2009, pp. 19599-19604.

"Structural Biasing Elements for In-Cell Histone Deacetylase Paralog Selectivity", Wong, et al., J. Am Chem. Soc., 2003, pp. 5586-5587.

"Second-Generation Histone Deacetylase 6 Inhibitors Enhance the Immunosuppressive Effects of Foxp3+ T-Regulatory Cells", Kalin, et al., Journal of Medicinal Chemistry, 2012, pp. 639-651.

"Discovery of Potent and Selective Histone Deacetylase Inhibitors via Focused Combinatorial Libraries of Cyclic a3ß-Tetrapetides", Olsen, et al., J. Med. Chem. Dec. 10, 2009, pp. 7836-7846.

* cited by examiner

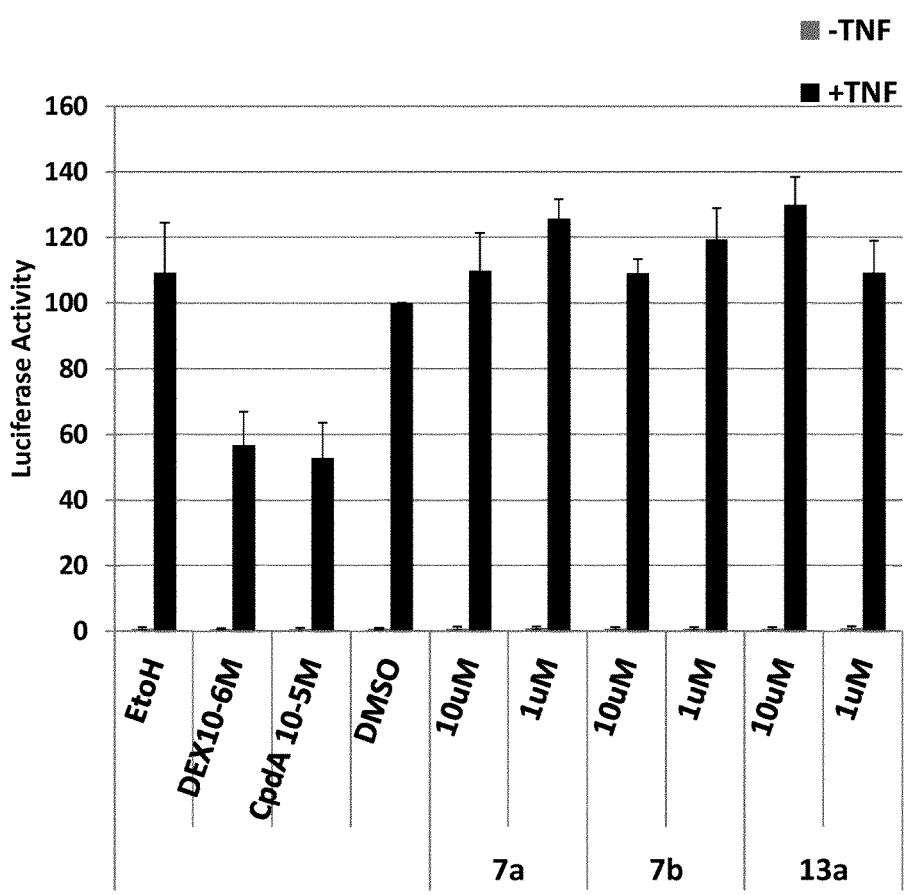
Figure 2 – continued

Figure 2 – continued 2
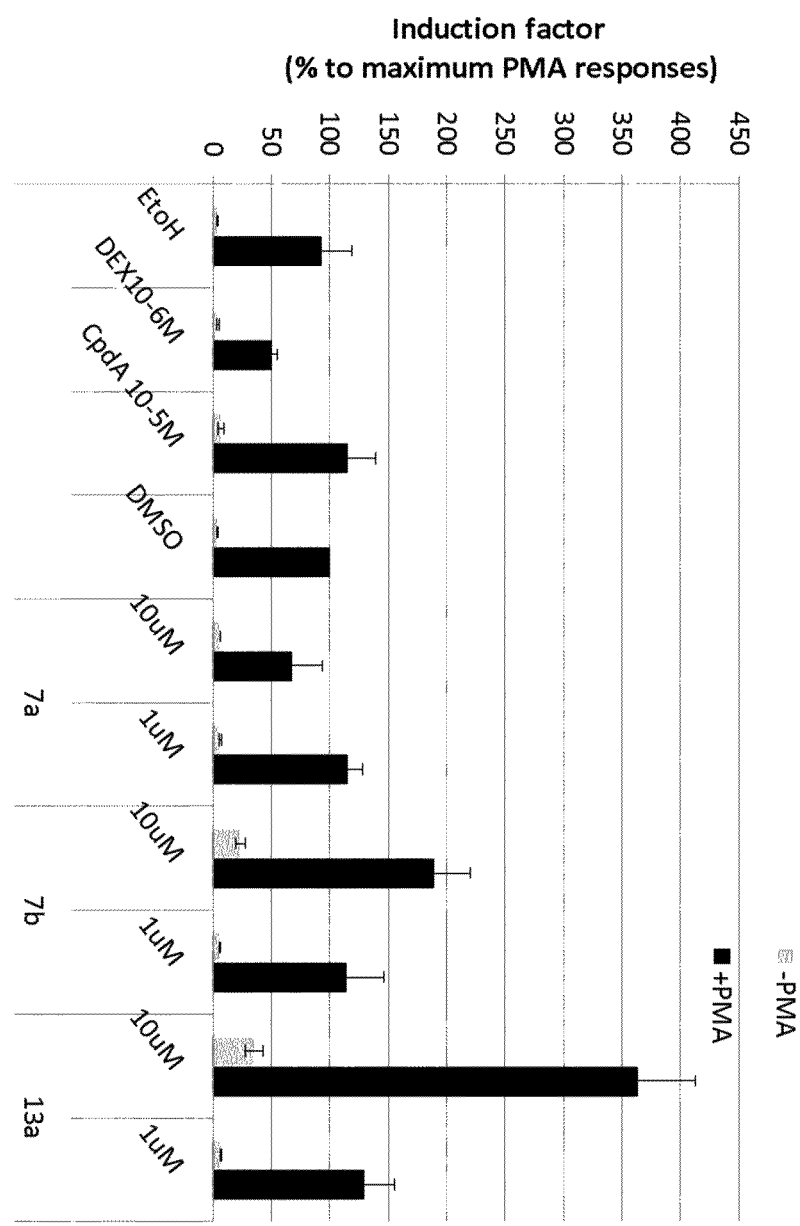

SELECTIVE HDAC6 INHIBITORS AND USES THEREOF

FIELD OF THE INVENTION

The present invention relates to Histone deacetylase 6 (HDAC6) inhibitors and compositions containing the same. Methods of treating diseases and conditions wherein inhibition of HDAC6 provides a benefit, like a cell proliferative disease, an autoimmune or inflammatory disorder, a neurodegenerative disease, or a combination thereof, also are disclosed.

BACKGROUND OF THE INVENTION

The enzymatic addition and removal of acetyl groups at specific lysine residues comprise important biochemical reactions with a significant impact on many cellular processes.[1] The addition of acetyl groups within histone proteins, the chief protein components of chromatin, is catalyzed by histone acetyltransferases (HAT), and histone deacetylases (HDAC) mediate the corresponding deacetylation reactions. The inhibition of the latter group of deacetylases has become a hot topic in medicinal chemistry, and the use of HDAC inhibitors (HDACIs) has found many applications with regard to cancer and CNS disorder therapies.[2] In general, HDACIs act on 11 zinc-dependent HDAC isozymes, which are divided into four groups: class I (HDACs 1, 2, 3, 8), class IIa (HDACs 4, 5, 7, 9), class IIb (HDACs 6, 10), and class IV (HDAC11).[3] The majority of known HDACIs primarily inhibit the class I enzymes, making them excellent candidates for cancer therapy applications, but other than class I HDACIs are normally required for the pursuit of non-oncology applications.[4] Another important issue relates to the potential toxicity of compounds inhibiting multiple isozymes, as acetylation is involved in the control of many cellular processes and inhibition of some isozymes may cause undesirable side effects. Thus, the design and development of isozyme-selective inhibitors has emerged as an important challenge within the search for novel HDACIs.[5]

In recent years, HDAC6 has been acknowledged as an attractive target for drug development,[6] and an increasing number of research teams are currently involved in the quest for new compounds endowed with HDAC6 inhibitory activity.[7] In addition to the potential of HDAC6-selective inhibitors for applications in the treatment of CNS disorders and neurodegenerative diseases, these compounds seem to provoke less side effects, hence the growing interest in their preparation.[8] An important milestone in that respect concerns the identification of Tubacin as a selective HDAC6 inhibitor, although the application of this compound is hampered by its poor drug likeness and cumbrous synthesis.[9] Since then, considerable advances have been made with regard to the preparation of new HDAC6 inhibitors, leading to an array of different molecular entities with improved chemical and pharmacological properties.[7] From a chemical viewpoint, many of these molecules comprise the typical HDACI basic structure accommodating an aromatic cap group (surface recognition domain), a linker and a zinc-binding hydroxamic acid unit. A major breakthrough was accomplished recently, involving the rational design and synthesis of Tubastatin A as a novel and selective HDAC6 inhibitor.[10] A later study by Kalin and coworkers observed that substitutions on the tetrahydrocarboline group of Tubastatin A analogues influence HDAC6 activity and selectivity.[11]

Recent progress in the discovery of selective HDAC6 inhibitors at a molecular level has also shown that a branched sp2-hybridised carbon atom in a-position with respect to the hydroxamate ZBG gives rise to a good HDAC6 selectivity profile.[12] This has been confirmed by different recently developed HDAC6 selective inhibitors with an N-hydroxybenzamide group in their molecular structure.[13] Further HDAC6 selective inhibitors have been explored in e.g. WO2011/011186, WO2011/106632, WO2013/134467 and WO2014/147178.

Despite these promising results, the structural requirements for selective inhibition remain largely unknown. Some compounds have been reported to display relative HDAC6 selectivity or preferential HDAC6 inhibition. Despite much effort, truly selective compounds are few, and the precise structural determinants required to achieve the selective inhibition of single HDAC isozymes generally remain undefined.

There is thus still a need in the art for novel HDACIs, and particularly selective HDAC6 inhibitors, that are useful in the treatment of diseases wherein HDAC inhibition provides a benefit, such as a cell proliferative disease, an autoimmune or inflammatory disorder, a neurodegenerative disease, a viral disease, malaria, or a combination thereof. Accordingly, a significant need exists in the art for efficacious compounds, compositions, and methods useful in the treatment of such diseases, alone or in conjunction with other therapies used to treat these diseases and conditions. The present invention is directed to meeting this need.

DETAILED DESCRIPTION

Figure 1:
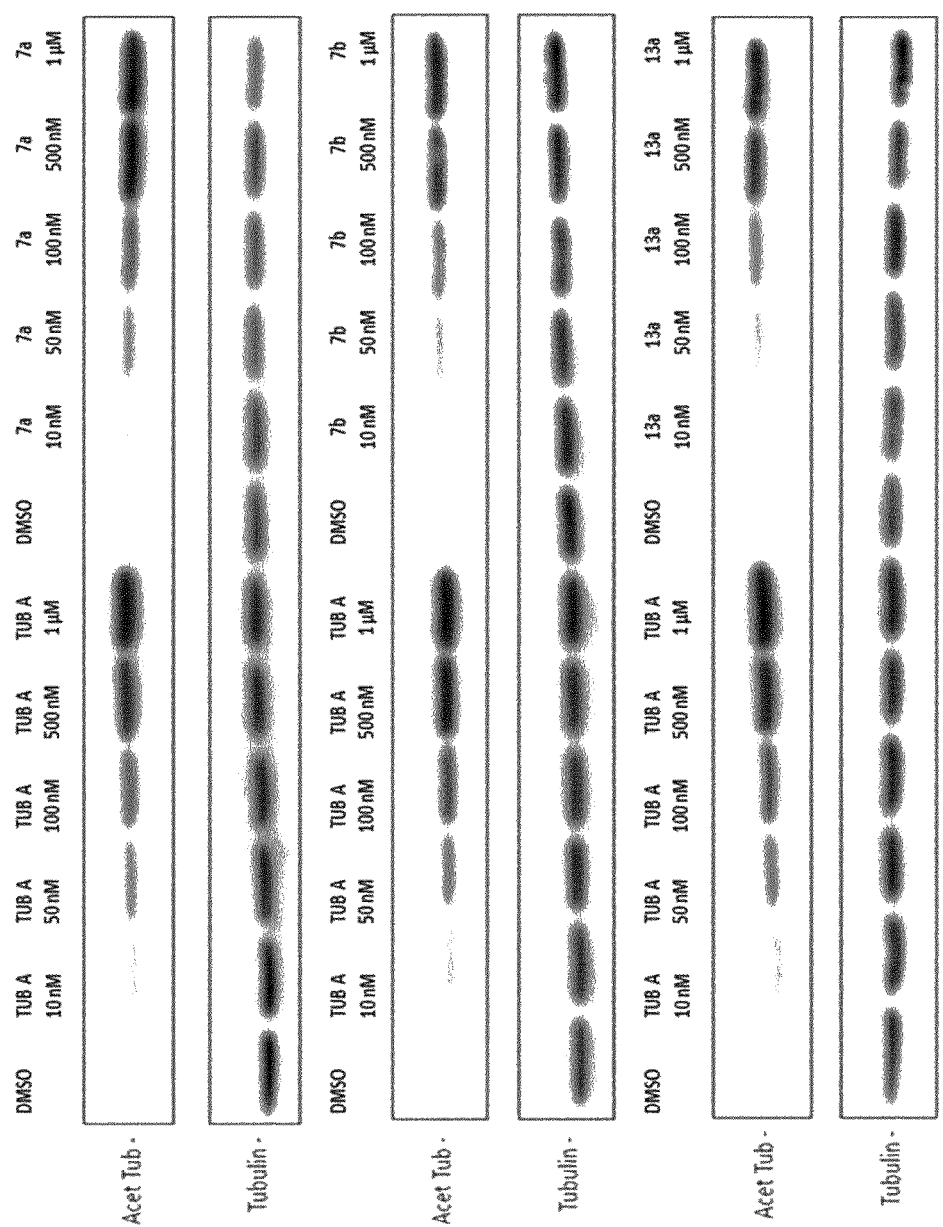
FIG. 1: Potency of inhibiting HDAC6 by compounds 7a, 7b and 13a in Neuro-2a cells. A. Cells were treated overnight with different concentrations of the HDAC6 inhibitors and blotted of the acetylation of α-tubulin. B. All compounds increase the acetylated α-tubulin at similar levels as Tubastatin A.

As used herein, the singular forms "a", "an", and "the" include both singular and plural referents unless the context clearly dictates otherwise. The terms "comprising", "comprises" and "comprised of" as used herein are synonymous with "including", "includes" or "containing", "contains", and are inclusive or open-ended and do not exclude additional, non-recited members, elements or method steps. The term "about" or "approximately" as used herein when referring to a measurable value such as a parameter, an amount, a temporal duration, and the like, is meant to encompass variations of +/−10% or less, preferably +1-5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed. Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any >3, >4, >5, >6 or >7 etc. of said members, and up to all said members. All references, and teachings specifically referred to, cited in the present specification are hereby incorporated by reference in their entirety. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. Reference throughout this specification to "one embodiment" or "an embodiment" means that a particular feature, structure or characteristic described in connection with the embodiment is included in at least one embodiment of the present invention.

Despite the therapeutic advantage of isoform-selective HDAC inhibitors, design of such inhibitors has been challenging due to the high sequence similarity within the active sites of the isoforms. The present invention provides inhibitors that are structurally distinct from known HDAC inhibitors and that are highly selective toward the HDAC6 isoform.

In particular, the present invention encompasses compounds having a benzothiophene as a template for cap group design. Benzothiophene is a heterocyclic aromatic compound with hydrophobic character allowing a good binding profile since the protein surface in the area of the cap group accommodates several hydrophobic amino acid residues. Benzothiophene has e.g. been used as a cap group in a cinnamyl hydroxamide scaffold for HDAC1-4 inhibitors.[14]

In a first embodiment, the invention provides a compound of formula I, or a stereoisomer, tautomer, racemic, salt, hydrate, or solvate thereof:

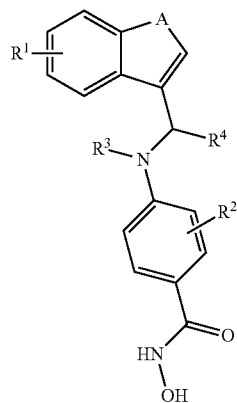

wherein

A is selected from NR, O and S;

R is selected from the group consisting of hydrogen, $C_{1-6}$alkyl, $C_{1-6}$alkenyl, $C_{1-6}$alkynyl, $C_{1-6}$haloalkyl, cycloalkyl, benzyl, and aryl;

$R^1$ is selected from the group consisting of hydrogen, halogen, $C_{1-6}$alkyl, $C_{1-6}$alkenyl, $C_{1-6}$alkynyl, $C_{1-6}$haloalkyl, amino, nitro, hydroxyl, cyano, cycloalkyl, aryl, heterocyclyl, heteroaryl, OR', SR', NR'R", and P(O)(OR')(OR");

R' and R" are independently selected from the group consisting of hydrogen, $C_{1-6}$alkyl, and aryl;

$R^2$ is selected from the group consisting of hydrogen, halogen, $C_{1-6}$alkyl, $C_{1-6}$alkenyl, $C_{1-6}$alkynyl, $C_{1-6}$haloalkyl, amino, nitro, hydroxyl, cyano, cycloalkyl, aryl, heterocyclyl, and heteroaryl;

$R^3$ is selected from hydrogen, $C_{1-6}$alkyl, cycloalkyl, aryl, heterocyclyl, and heteroaryl;

wherein said $C_{1-6}$alkyl is optionally substituted with halogen, amino, nitro, cycloalkyl, aryl, heterocyclyl, or heteroaryl; and $R^4$ is selected from the group consisting of hydrogen, $C_{1-6}$alkyl, $C_{1-6}$alkenyl, $C_{1-6}$alkynyl, $C_{1-6}$ haloalkyl, cycloalkyl, aryl, heterocyclyl, and heteroaryl.

The invention also relates to metabolites, pre- and prodrugs of the compounds of formula I.

In a preferred embodiment, the present invention provides those compounds of formula I wherein A is NR or S. In a further embodiment, R is selected from hydrogen and $C_{1-6}$alkyl; in particular R is hydrogen. In a particularly preferred embodiment, the present invention provides those compounds of formula I wherein A is S.

In a particular embodiment, the present invention provides compounds of formula I wherein at least one of R' and R" are hydrogen; in particular wherein R' and R" are both hydrogen. In another particular embodiment, the present invention provides compounds of formula I wherein $R^1$ is selected from the group consisting of hydrogen, halogen, $C_{1-6}$alkyl, $C_{1-6}$alkenyl, $C_{1-6}$alkynyl, $C_{1-6}$haloalkyl, amino, nitro, hydroxyl, cyano, cycloalkyl, aryl, heterocyclyl, and heteroaryl. In particular wherein $R^1$ is selected from hydrogen, halogen, and aryl. In another embodiment, $R^1$ is selected from hydrogen and halogen.

In another particular embodiment, the present invention provides compounds of formula I wherein $R^2$ is selected from the group consisting of hydrogen, halogen, $C_{1-6}$alkyl, amino, and nitro. In particular wherein $R^2$ is hydrogen or methyl; more in particular wherein $R^2$ is hydrogen.

In another particular embodiment, the present invention provides compounds of formula I wherein $R^3$ is selected from hydrogen or $C_{1-6}$alkyl optionally substituted with halogen, amino, nitro, cycloalkyl, aryl, heterocyclyl, or heteroaryl. In particular wherein $R^3$ is selected from hydrogen and $C_{1-6}$alkyl substituted with phenyl.

In a preferred embodiment, the present invention provides compounds of formula I wherein $R^1$ is hydrogen or halogen; and $R^2$ is hydrogen.

In yet another embodiment, the present invention provides compounds of formula I wherein $R^4$ is hydrogen or $C_{1-6}$alkyl; in particular hydrogen.

In another further preferred embodiment, the present invention provides compounds selected from the group consisting of

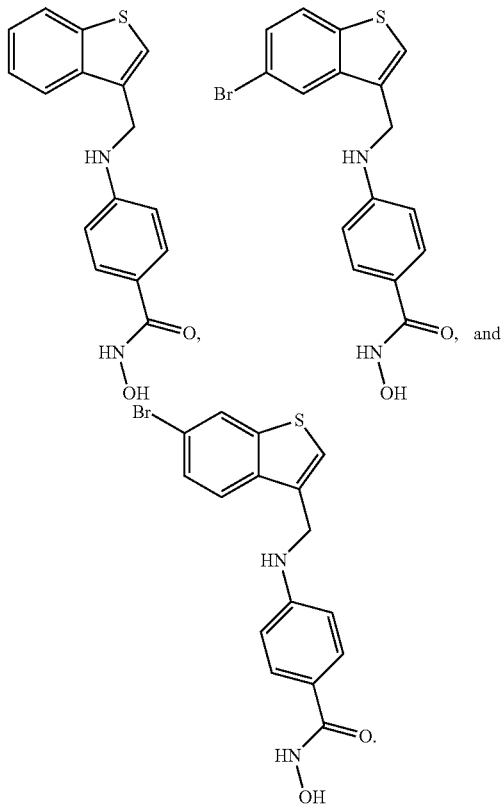

It is a further object of the invention to provide compounds of formula II

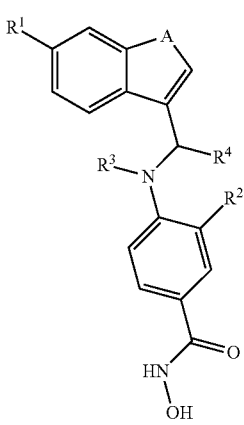

wherein $R^1$, $R^2$, $R^3$ and $R^4$ are as described for the compounds of formula I.

It is also an object of the invention to provide compounds of formula III

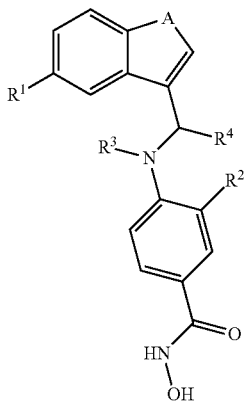

wherein $R^1$, $R^2$, $R^3$ and $R^4$ are as described for the compounds of formula I.

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 20 carbon atoms. Alkyl groups may be linear or branched. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl (also shortened as Me), ethyl, n-propyl (also shortened as nPr), i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers.

The term "alkenyl", as used herein, unless otherwise indicated, means straight-chain[1] or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like.

The term "alkynyl", as used herein, unless otherwise indicated, means straight-chain or branched-chain hydrocarbon radicals containing at least one carbon-carbon triple bond. Examples of alkynyl radicals include ethynyl, propynyl, butynyl, pentynyl, hexynyl, and the like.

The term "cycloalkyl" by itself or as part of another substituent is a cyclic alkyl group, that is to say, a monovalent, saturated, or unsaturated hydrocarbyl group having 1, 2, or 3 cyclic structure. Cycloalkyl includes all saturated or partially saturated (containing 1 or 2 double bonds) hydrocarbon groups containing 1 to 3 rings, including monocyclic, bicyclic, or polycyclic alkyl groups. Cycloalkyl groups may comprise 3 or more carbon atoms in the ring and generally, according to this invention comprise from 3 to 15 atoms, even more preferably cycloalkyl is monocyclic and contains from 3 to 8 atoms. The further rings of multi-ring cycloalkyls may be either fused, bridged and/or joined through one or more spiro atoms. Cycloalkyl groups may also be considered to be a subset of homocyclic rings discussed hereinafter. Examples of cycloalkyl groups include but are not limited to cyclopropyl, cyclobutyl, cyclopentyl, cyclohexyl, cycloheptyl, cyclooctyl, cyclononyl, adamantanyl, bicyclo(2.2.1)heptanyl and cyclodecyl with cyclopropyl, cyclopentyl, cyclohexyl, adamantanyl, and bicyclo(2.2.1)heptanyl being particularly preferred. When the suffix "ene" is used in conjunction with a cyclic group, hereinafter also referred to as "Cycloalkylene", this is intended to mean the cyclic group as defined herein having two single bonds as points of attachment to other groups. Cycloalkylene groups of this invention preferably comprise the same number of carbon atoms as their cycloalkyl radical counterparts.

The terms "heterocyclyl" or "heterocyclo" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. Preferably, heterocyclyl is mono- or bicyclic group containing from 3 to 10 carbon atoms wherein 1 to 3 carbon atoms have been replaced by nitrogen, oxygen and/or sulfur. The heterocyclic group may be attached at any heteroatom or carbon atom of the ring or ring system, where valence allows. The rings of multi-ring heterocycles may be fused, bridged and/or joined through one or more spiro atoms. Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, terehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl. In a preferred embodiment, heterocyclyl refers to a monocyclic ring having 3 to 9 carbon atoms and 1 to 4 heteroatoms.

The term "halo" or "halogen" as a group or part of a group is generic for fluoro, chloro, bromo, or iodo.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl, and the like.

The term "aryl" as used herein refers to a polyunsaturated, aromatic hydrocarbyl group having a single ring (i.e. phenyl) or multiple aromatic rings fused together (e.g. naphthalene or anthracene) or linked covalently, typically containing 6 to 10 atoms per ring; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1-2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cyloheptenyl, and 1-, 2-, 3-, 4-, or 5-pyrenyl. Preferred aryl groups have a single ring of 5 to 10 atoms, such as phenyl (sometimes abbreviated herein as "Ph").

"Benzyl" (sometimes abbreviated herein as "Bn") refers to substituent consisting of a phenyl group linked through a methylene group (i.e. having the formula $C_6H_5CH_2$—).

Where a carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, benzopyranyl, 1(4H)-benzopyranyl, 1(2H)-benzopyranyl, 3,4-dihydro-1(2H)-benzopyranyl, 3,4-dihydro-1(2H)-benzopyranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl. In a preferred embodiment, heteroaryl refers to a monocyclic aromatic ring having 3 to 9 carbon atoms and 1 to 3 heteroatoms.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkenyl groups as defined above and alkynyl groups as defined above, respectively, are divalent radicals having single bonds for attachment to two other groups, they are termed "alkenylene" and "alkynylene" respectively. Similarly, an arylene group refers to a bivalent group derived from an arene by removal of a hydrogen atom from each of two ring carbon atoms. A synonym is arenediyl group.

The present invention relates to compounds having the Formulas as disclosed herein, including derivatives, prodrugs and pharmaceutically acceptable salts thereof, compositions and kits comprising such compounds, methods for making, and methods of use in treating histone deacetylase-associated disorders.

In a preferred embodiment, the compounds of the present invention are used as HDAC inhibitors, in particular as HDAC6 inhibitors, more in particular as selective HDAC6 inhibitors. In a particular embodiment the present invention provides a compound of formula I to III for use as a medicine, in particular a human or veterinary medicine. In a further embodiment, the present invention provides a composition comprising a compound as described herein. The composition may be a pharmaceutical composition comprising a compound of the invention and one or more pharmaceutically acceptable carriers or excipients.

In a particular embodiment, the present invention provides a compound of formula I, II and/or III for use in the treatment and/or prevention of a HDAC-associated disease, in particular a HDAC6-associated disease.

As used herein, the terms "treat," "treating," "treatment," and the like refer to eliminating, reducing, relieving, reversing, and/or ameliorating a disease or condition and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition, "treatment" therefore also includes relapse prophylaxis or phase prophylaxis. By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control. The term "treat" and synonyms contemplate administering a therapeutically effective amount of a compound of the invention to an individual in need of such treatment. A treatment can be orientated symptomatically, for example, to suppress symptoms. It can be effected over a short period, be oriented over a medium term, or can be a long-term treatment, for example within the context of a maintenance therapy.

The term "prevention" as used herein refers to reducing the probability that a disease or condition will develop in a subject who does not have, but is at risk of or is susceptible to developing the disease or condition. Prevention does not necessarily imply that none of the subjects will develop the disease or condition, but rather that they have a reduced risk thereto.

In a further embodiment the invention relates to the use of compounds of the invention in a method of treating a histone deacetylase (HDAC)-associated disease, comprising: (a) providing at least one compound of Formula I to III as described herein; and (b) administering a composition to a subject with symptoms of the HDAC-associated disease, comprising a therapeutic amount of the HDAC inhibitor compound and a pharmaceutically acceptable carrier, wherein the therapeutic amount is effective to inhibit the activity of at least the HDAC6 isoform and in treating the symptoms of the HDAC-associated disease. A HDAC-associated disease is characterized by lower level of acetylated tubulin in cells isolated from the subject with symptoms of the HDAC-associated disease relative to the level of acetylated tubulin in cells isolated from a healthy subject. More specific, the HDAC-associated disease is selected from the group consisting of a cell proliferative disease, an autoimmune or inflammatory disorder, a neurodegenerative disease, a viral disease, malaria, or a combination thereof. In a further embodiment, the HDAC-associated disease is selected from the group consisting of a cell proliferative disease, an autoimmune or inflammatory disorder, a neurodegenerative disease, or a combination thereof.

In a particular embodiment, the HDAC-associated disease is a cell proliferative disease, selected from cancer and any metastasis thereof. According to another embodiment, the cell proliferative disease is a cancer, selected from the group consisting of an ovarian cancer, a prostate cancer, a lung cancer, an acute myeloid leukemia, a multiple myeloma, a bladder carcinoma, a renal carcinoma, a breast carcinoma, a colorectal carcinoma, a neuroblastoma, a melanoma, a gastric cancer, or a combination thereof. According to another embodiment, the autoimmune or inflammatory disorder is selected from the group consisting of rheumatoid arthritis, psoriasis, inflammatory bowel disease, multiple sclerosis, systemic lupus erythematosus, airway hyperresponsiveness, Crohn's disease, ulcerative colitis, or a combination thereof. Hence, in a specific embodiment, the compounds of the invention are used for treating oncological disorders in a patient. Methods of using the disclosed compounds to inhibit or kill tumor cells, to inhibit HDAC6, and to augment tumor inflammatory responses are also disclosed. In another particular embodiment, the present invention provides a method for inhibiting the proliferation of cells, in particular inhibiting tumor growth, said method comprising administering a compound of the invention, or a composition comprising it, to a subject.

According to another embodiment, the neurodegenerative disorder is selected from the group consisting of cerebral ischemia, Huntington's disease, amyotrophic lateral sclerosis, spinal muscular atrophy, Parkinson's disease, Alzheimer's disease, peripheral nervous system disorder and other hereditary axonopathies, or a combination thereof.

According to another embodiment, the HDAC-associated disease is an inflammatory disease, such as arthritis, in particular rheumatoid arthritis.

The present methods also encompass administering a second therapeutic agent to the individual in addition to a compound of the invention. The second therapeutic agent is selected from agents, such as drugs and adjuvants, known as useful in treating the disease or condition afflicting the individual, such as a cell proliferative disease, an autoimmune or inflammatory disorder, and/or a neurodegenerative disease. For example a chemotherapeutic agent and/or radiation known as useful in treating a particular cancer. The present invention includes methods for treating cancer comprising administering to an individual in need thereof a compound according to the invention and one or more additional anticancer agents or pharmaceutically acceptable salts thereof. The compound of the invention and the additional anticancer agent can act additively or synergistically. Suitable anticancer agents include, but are not limited to, gemcitabine, capecitabine, methotrexate, taxol, taxotere, mereaptopurine, thioguanine, hydroxyurea, cyclophosphamide, ifosfamide, nitrosoureas, mitomycin, dacarbazine, procarbizine, etoposide, teniposide, campatheeins, bleomycin, doxorubicin, idarubicin, daunorubicin, dactinomycin, plicamycin, mitoxantrone, L-asparaginase, doxorubicin, epirubicin, 5-fluorouracil (5-FU), taxanes (such as docetaxel and paclitaxel), leucovorin, levamisole, irinotecan, estramustine, etoposide, nitrogen mustards, BCNU, nitrosoureas (such as carmustine and lomustine), platinum complexes (such as cisplatin, carboplatin and oxaliplatin), imatinib mesylate, hexamethylmelamine, topotecan, tyrosine kinase inhibitors, tyrphostins herbimycin A, genistein, erbstatin, and lavendustin A. As used herein a subject is a human or animal, in particular human.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. In certain examples, compounds and compositions disclosed herein can be locally administered at one or more anatomical sites, such as e.g. sites of unwanted cell growth (such as a tumor site or benign skin growth, e.g., injected or topically applied to the tumor or skin growth), optionally in combination with a pharmaceutically acceptable carrier such as an inert diluent.

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

EXAMPLES

General Synthesis Scheme

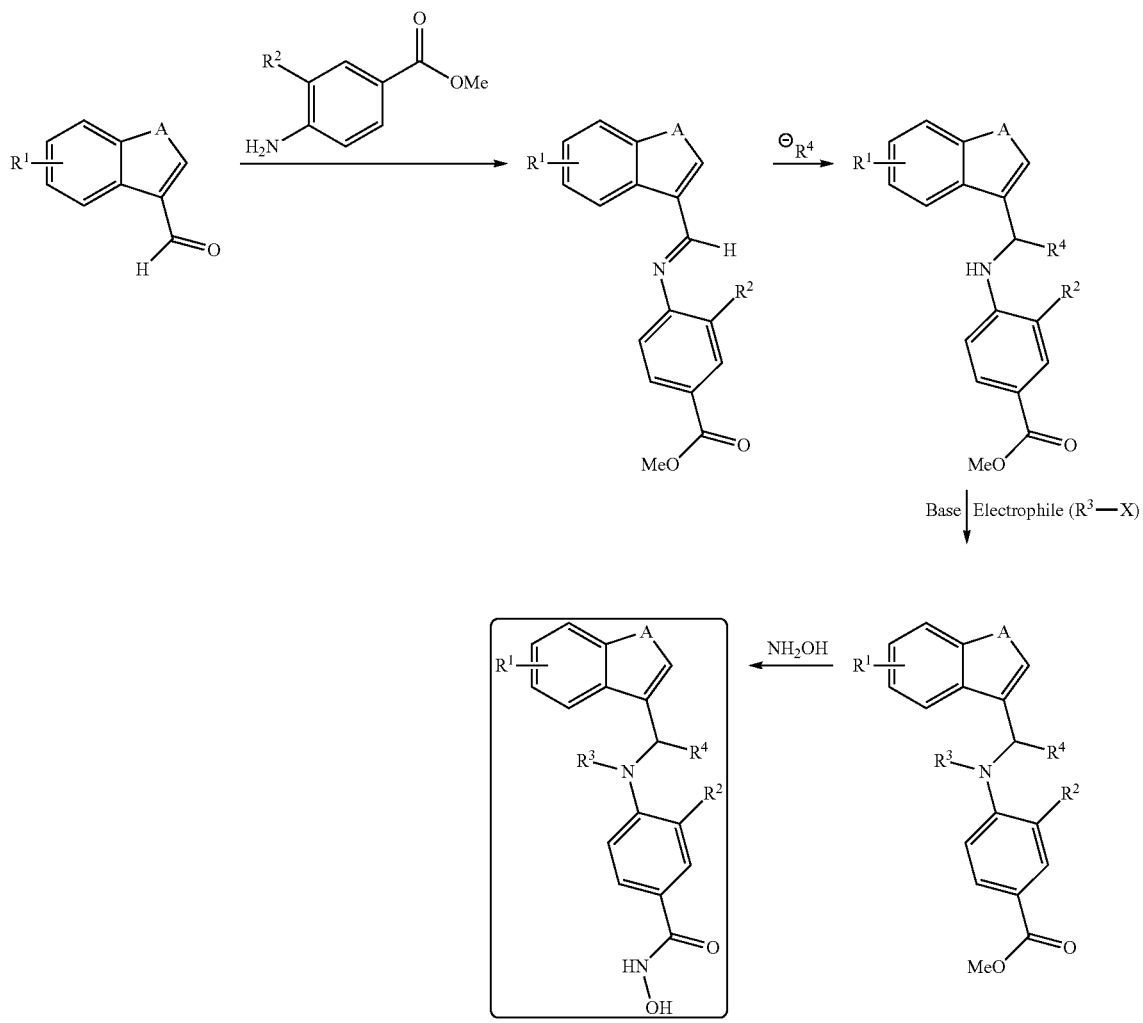

The foregoing general synthesis scheme wherein A, $R^1$, $R^2$, $R^3$, and $R^4$ are defined in accordance with the present invention is further detailed for the benzothiophenes (i.e. compounds wherein A=S) herein below.

The 3-[(4-hydroxycarbamoylphenyl)aminomethyl]benzothiophenes 2 were synthesized and evaluated. The conjunction between the methyl 4-aminobenzoate derivative and benzothiophene was based on a straightforward synthetic pathway and characterized by the presence of a nitrogen atom as an anchor point for further derivatization. Furthermore, a short linker unit between benzothiophene and the benzenehydroxamic acid scaffold should account for optimal interactions with the surface of the enzyme. In order to explore the theoretical potential of these new compounds in silico, a set of representative structures was subjected to docking studies.

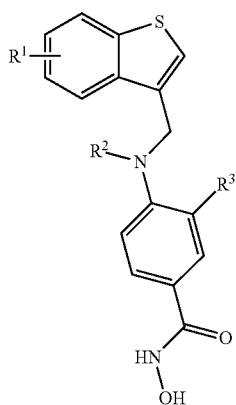

2

$R^1$ = H, Ph
$R^2$ = H, Bn
$R^3$ = H, Me

Compounds of formula 2 were subjected to docking studies in a homology model of HDAC6.

These studies revealed that expansion of the cap group ($R^1$=Ph) and the introduction of a benzylic group on the secondary amine ($R^2$=Bn) could result in a more complete occupation of the binding pocket (results not shown). Thus, the focus was pointed toward the synthesis of these structures (Scheme 1 and 2, Table 1). In addition, the indole counterpart of 'mother' structure 2 was synthesized to verify the hypothesis that the protein surface close to the cap group preferably binds to a more hydrophobic scaffold (benzothiophene vs. indole). Finally, also 3-[(4-hydroxycarbamoyl-2-methylphenyl)aminomethyl]benzothiophene was synthesized to study the influence of a methyl group in the linker.

The synthesis deployed the commercially available benzothiophene-3-carbaldehyde 3a and 5-bromobenzothiophene-3-carbaldehyde 3b as substrates (Scheme 1). First, 5-phenylbenzothiophene-3-carbaldehyde 4 was obtained via a Suzuki-Miyaura cross-coupling using 5-bromobenzothiophene-3-carbaldehyde, tetrakis(triphenyl-phosphine)palladium, phenylboronic acid and sodium carbonate in a toluene/ethanol/water (2/1/1) mixture. Reductive amination of carbaldehydes 3a-b and 4 employing methyl 4-aminobenzoate or methyl 4-amino-3-methylbenzoate and sodium cyanoborohydride resulted in the synthesis of methyl 4-aminobenzoate esters 5a-d.[14] These secondary amines 5a-c were further N-benzylated by using benzylbromide and sodium hydride in DMF and gave 3-[N-benzyl-N-(4-methoxycarbonylphenyl)aminomethyl]benzothiophenes 6a-c. As last step, hydroxamic acids 7a-d and 8a-c were synthesized by converting methyl esters 5a-d and 6a-c upon treatment with an excess of hydroxyl amine and potassium hydroxide in THF.

The synthesis of the second group of substituted benzothiophene-based hydroxamic acids commenced with the bromination of benzothiophene-3-carbaldehyde 3a in acetonitrile to obtain 6-bromobenzothiophene-3-carbaldehyde 9 as the main isomer (60%, $^1$H-NMR, $CDCl_3$) in an isolated yield of 40%.[15] Suzuki-Miyaura cross-coupling of 6-bromobenzothiophene-3-carbaldehyde 9 with phenylboronic acid, tetrakis(triphenyl-phosphine)palladium and sodium carbonate gave 6-phenylbenzothiophene-3-carbaldehyde 10 in a high yield (96%). Both carbaldehydes 9 and 10 were consecutively converted into methyl 4-aminobenzoate ester 11a-b by means of reductive amination. The N-benzylated counterparts 12a-b of secondary amines 11a-b were obtained through nucleophilic substitution employing benzylbromide. Treatment of esters 11a-b and 12a-b with hydroxyl amine eventually afforded hydroxamic acids 13a-b and 14a-b. (Scheme 2). In summary, application of the strategies as depicted in Scheme 1 and 2 resulted in a small set of eleven novel benzothiophene-based hydroxamic acids as potentially interesting molecules in the framework of HDAC6 inhibition.

Scheme 1.

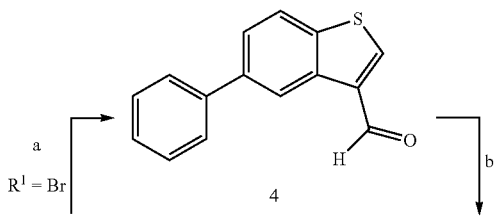

a
$R^1$ = Br

4 b

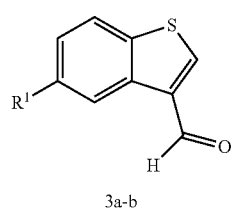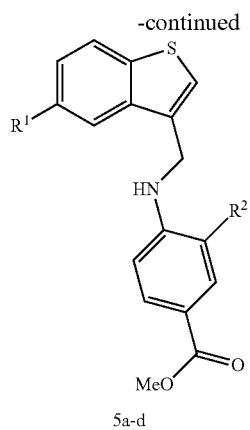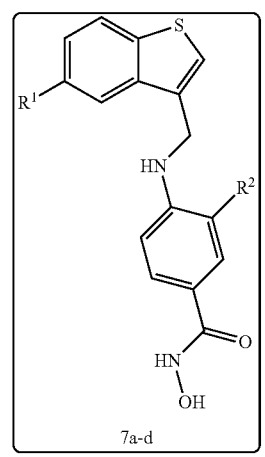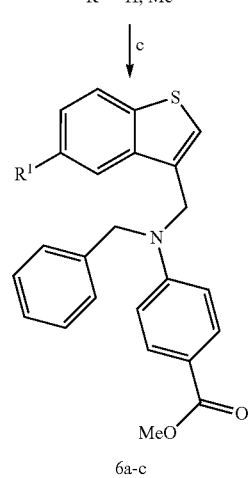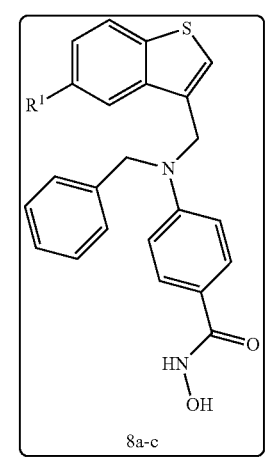

a: phenylboronic acid (2 equiv), Na$_2$CO$_3$ (6.5 equiv), Pd(PPh$_3$)$_4$ (4 mol %), toluene/ethanol/H$_2$O (2/1/1), Δ, 8 h, N$_2$, 72%.
b: methyl 4-aminobenzoate or methyl 4-amino-3-methylbenzoate (1.2 equiv), glacial acetic acid (5 equiv), ethanol or ethanol/CH$_2$Cl$_2$, Δ, 1 h -> NaCNBH$_3$ (3 equiv), 0° C. -> r.t., 1 h, 50-75%.
c: NaH (60% in mineral oil, 1.2 equiv), DMF, r.t., 30′ -> benzylbromide (2 equiv), KI (5 mg), 2 h, r.t., 65-79%.
d: NH$_2$OH (50% in H$_2$O, 100 equiv), KOH (4M in MeOH, 50 equiv), THF, r.t., 10′, 13-85%.

Several attempts to obtain the indole-containing methyl 4-aminobenzoate ester 17, starting from indole-3-carbaldehyde 15, using the procedures described above failed. However, a Dean Stark-mediated procedure using a catalytic amount of p-toluenesulfonic acid did effect the desired imination, and aldimine 16 was obtained after recrystallization. NaBH$_4$-assisted reduction of the latter imine then afforded the indole-based methyl 4-aminobenzoate ester 17. Finally, ester to hydroxamic acid conversion produced the desired target structure 18 in a good yield (Scheme 3).

Scheme 2.

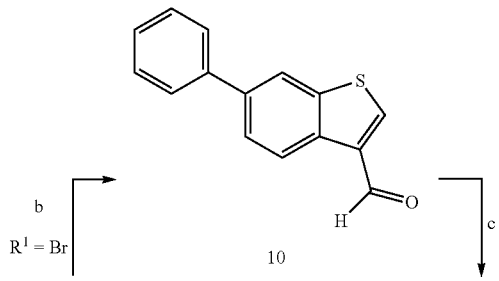

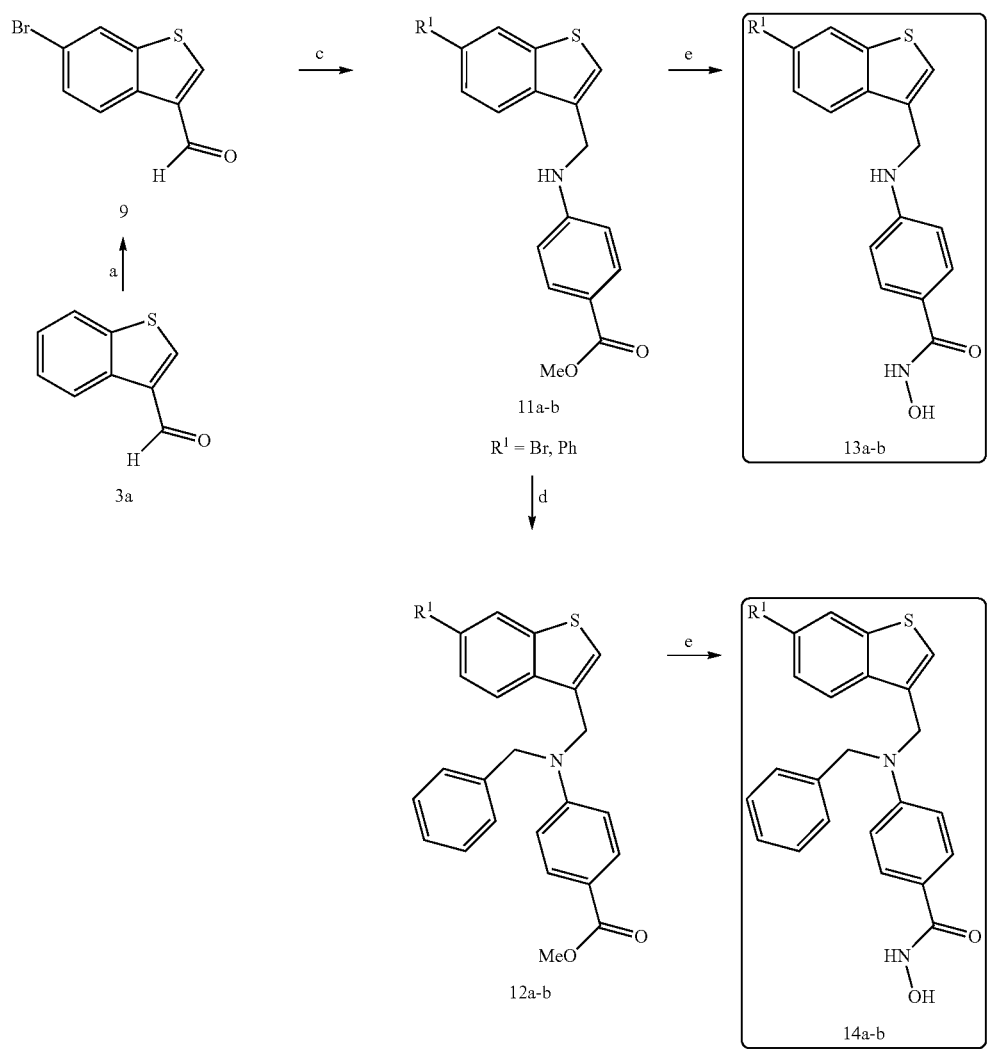
a: Br₂ (5 equiv), CH₃CN, r.t., 18 h, 40%.
b: phenylboronic acid (2 equiv), Na₂CO₃ (6.5 equiv), Pd(PPh₃)₄ (4 mol %), toluene/ethanol/H₂O (2/1/1), Δ, 8 h, N₂, 96%.
c: methyl 4-aminobenzoate (1.2 equiv), glacial acetic acid (5 equiv), ethanol, Δ, 1 h -> NaCNBH₃ (3 equiv), 0° C. -> r.t., 1 h, 50-66%.
d: NaH (60% in mineral oil, 1.2 equiv), DMF, r.t., 30' -> benzylbromide (2 equiv), KI (5 mg), 2 h, r.t., 87-91%.
e: NH₂OH (50% in H₂O, 100 equiv), KOH (4M in MeOH, 50 equiv), THF, r.t., 10', 56-80%.
Scheme 3.
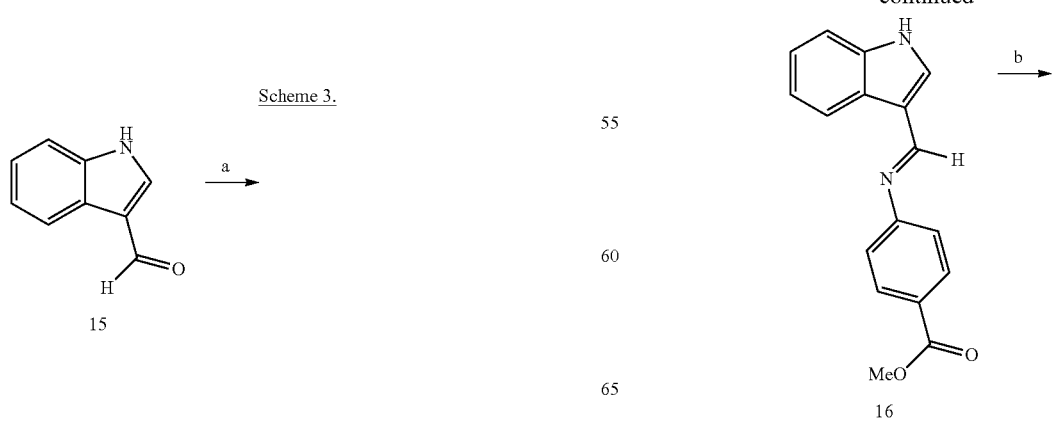

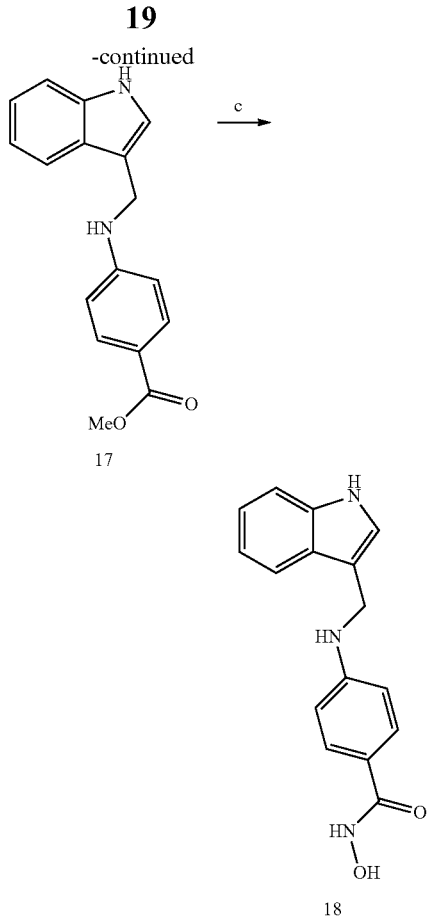

a: methyl 4-aminobenzoate (1.2 equiv), p-toluenesulfonic acid monohydrate (0.05 equiv), toluene, Dean Stark, 18 h, 85%.
b: NaBH$_4$ (5 equiv), MeOH, Δ, 90′, 88%.
c: NH$_2$OH (50% in H$_2$O, 100 equiv), KOH (4M in MeOH, 50 equiv), THF, r.t., 10′, 77%.

$^1$H NMR spectra were recorded at 300 MHz (JEOL ECLIPSE+) or 400 MHz (Bruker Avance III) with CDCl$_3$ or [D$_6$]DMSO as solvent and tetramethylsilane as internal standard. $^{13}$C NMR spectra were recorded at 75 MHz (JEOL ECLIPSE+) or 100.6 MHz (Bruker Avance III) with CDCl$_3$ or [D$_6$]DMSO as solvent and tetramethylsilane as internal standard. Mass spectra were obtained with a mass spectrometer Agilent 1100, 70 eV. IR spectra were measured with a Spectrum One FT-IR spectrophotometer. High resolution electron spray (ES) mass spectra were obtained with an Agilent Technologies 6210 series time-of-flight instrument. Melting points of crystalline compounds were measured with a Büchi 540 apparatus or with a Kofler Bench, type WME Heizbank of Wagner & Munz. The purity of all tested compounds was assessed by HRMS analysis and/or HPLC analysis, confirming a purity of ≥95%.

Synthesis of 6-bromobenzothiophene-3-carbaldehyde 9[15]

Benzothiophene-3-carbaldehyde (811 mg, 5 mmol, 1 equiv) 3a was dissolved in acetonitrile (15 mL) and to this solution was slowly added bromine (1.29 mL, 25 mmol, 5 equiv). The resulting reaction mixture was stirred at room temperature for 18 hour after which it was partitioned between an aqueous sodium bicarbonate solution (50 mL) and EtOAc (50 mL). To this biphasic solution was added dropwise, under vigorous stirring, a saturated aqueous sodium thiosulfate solution until discoloration of the organic medium. The organic layer was separated, and the aqueous layer was extracted with EtOAc (25 mL). The organic fractions were combined, dried (MgSO$_4$), filtered and concentrated under vacuum. Purification through column chromatography (R$_f$ 0.14, EtOAc/PE: 1/13) yielded 6-bromobenzothiophene-3-carbaldehyde 9 (482 mg, 2 mmol, 40%) as a white powder.

9: 6-bromobenzothiophene-3-carbaldehyde 40% as white powder; R$_f$ 0.14 (EtOAc/PE: 1/13); m.p 111° C.; $^1$H-NMR (400 MHz, CDCl$_3$): δ=7.63 (dd, J=8.7, 1.7 Hz, 1H); 8.04 (d, J=1.7 Hz, 1H); 8.30 (s, 1H); 8.56 (d, J=8.7 Hz, 1H); 10.12 (s, 1H); $^{13}$C-NMR (100.6 MHz, CDCl$_3$): δ=120.2, 125.0, 125.9, 129.6, 134.0, 136.1, 141.8, 143.2 and 185.1; IR (cm$^{-1}$): ν=1662 (C=O); Elemental Analysis Calcd (%) for C$_9$H$_5$BrOS: C 44.84 H 2.09; Found: C 45.17 H 1.71.

Synthesis of 5- and 6-phenylbenzothiophene-3-carbaldehyde 4 and 10

The synthesis of 5-phenylbenzothiophene-3-carbaldehyde 4 will be used as an example for the synthesis of 5- and 6-phenylbenzothiophene-3-carbaldehydes 4 and 10. 5-Bromobenzothiophene-3-carbaldehyde 3b (482 mg, 2 mmol, 1 equiv) was dissolved in toluene (15 mL) and to this solution were added an aqueous solution of sodium carbonate (7 mL, 2M) and a solution of phenylboronic acid (488 mg, 4 mmol, 2 equiv) in ethanol (7 mL). This mixture was flushed with nitrogen for 10 minutes before tetrakis(triphenylphosphine) palladium(0) (92 mg, 0.08 mmol, 0.04 equiv) was added and the reaction mixture was heated to its boiling temperature for 8 hour. The reaction mixture was poured in to brine (20 mL) and three times extracted with EtOAc (20 mL). The combined organic fraction was thereafter three times washed with brine (15 mL), dried (MgSO$_4$), filtered and evaporated under vacuum. Purification through column chromatography (R$_f$ 0.35, EtOAc/PE 1/5) yielded 5-phenylbenzothiophene-3-carbaldehyde 4 (343 mg, 1.44 mmol, 72%) as an orange powder.

4: 5-phenylbenzothiophene-3-carbaldehyde 72% as orange powder; R$_f$ 0.35 (EtOAc/PE 1/5); m.p. 102° C.; $^1$H-NMR (300 MHz, CDCl$_3$): δ=7.36-7.41 (m, 1H); 7.46-7.51 (m, 2H); 7.69-7.72 (m, 3H); 7.94 (d, J=8.3 Hz, 1H); 8.35 and 8.92 (2×s, 2×1H); 10.17 (s, 1H); $^{13}$C-NMR (75 MHz, CDCl$_3$): δ=122.7, 123.3, 125.9, 127.6, 127.7, 129.0, 135.9, 136.7, 139.5, 139.8, 140.8, 144.0 and 185.5; IR (cm$^{-1}$): ν=1671 (C=O); MS (70 eV): m/z (%)=239 (35) [M$^+$+H]; HRMS (ESI) Anal. Calcd. for C$_{15}$H$_{11}$OS 239.0525 [M$^+$+H] Found 239.0524.

10: 6-phenylbenzothiophene-3-carbaldehyde 96% as orange powder; R$_f$ 0.20 (EtOAc/PE 1/13); m.p. 94° C.; $^1$H-NMR (400 MHz, CDCl$_3$): δ=7.37-7.41 (m, 1H); 7.46-7.50 (m, 2H); 7.65-7.68 (m, 3H); 7.76 (dd, J=8.4, 1.4 Hz, 1H); 8.08 (d, J=1.4 Hz, 1H); 8.33 (s, 1H); 8.72 (d, J=8.4 Hz, 1H); 10.16 (s, 1H); $^{13}$C-NMR (100.6 MHz, CDCl$_3$): δ=120.6, 125.0, 125.8, 127.4, 127.7, 129.0, 134.2, 136.4, 139.6, 140.5, 141.3, 143.2 and 185.4; IR (cm$^{-1}$): ν=1662 (C=O); MS (70 eV): m/z (%)=239 (100) [M$^+$+H]; HRMS (ESI) Anal. Calcd. for C$_{15}$H$_{11}$OS 239.0525 [M$^+$+H] Found 239.0524.

Synthesis of methyl 4-aminobenzoate esters 5a-d and 11a-b

The synthesis of 3-[(4-methoxycarbonylphenyl)aminomethyl]benzothiophene 5a will be used as an example for the synthesis of secondary amines 5a-d and 11a-b. Benzothiophene-3-carbaldehyde 3a (406 mg, 2.5 mmol, 1 equiv) was dissolved in ethanol (15 mL) and to this solution were added glacial acetic acid (751 mg, 12.5 mmol, 5 equiv) and methyl 4-aminobenzoate (454 mg, 3 mmol, 1.2 equiv). This reaction mixture was stirred for one hour at refluxing conditions after which it was cooled to 0° C. Sodium cyanoborohydride (471 mg, 7.5 mmol, 3 equiv) was added and the reaction mixture was allowed to warm to room temperature. After one hour the mixture was poured in to brine (15 mL) and three times extracted with EtOAc (15 mL). The combined organic fraction was thereafter three times washed with brine (15 mL), dried (MgSO$_4$), filtered and evaporated under vacuum. Purification through recrystallization from ethanol yielded 3-[(4-methoxycarbonylphenyl)aminomethyl]-benzothiophene 5a (520 mg, 1.75 mmol, 70%) as a white powder. For secondary amine 5b a solvent mixture of ethanol/CH$_2$Cl$_2$ (1/1) was used as solvent for the reaction.

5a: 3-[(4-methoxycarbonylphenyl)aminomethyl]benzothiophene 70% as white powder; recrystallization from EtOH; m.p. 127° C.; $^1$H-NMR (300 MHz, CDCl$_3$): δ=3.84 (s, 3H); 4.48 (s(broad), 1H); 4.58 (d, J=5.0 Hz, 2H); 6.62 (d, J=8.8 Hz, 2H); 7.32 (s, 1H); 7.35-7.43, 7.73-7.81 and 7.86-7.90 (3×m, 2H, 1H and 3H); $^{13}$C-NMR (75 MHz, CDCl$_3$): δ=42.2, 51.7, 111.8, 119.0, 121.7, 123.2, 124.1, 124.4, 124.8, 131.7, 132.8, 137.8, 141.0, 151.7 and 167.4; IR (cm$^{-1}$): ν=3379 (NH); 1685 (C=O); MS (70 eV): m/z (%)=296 (100) [M$^-$–H]; HRMS (ESI) Anal. Calcd. for C$_{17}$H$_{14}$NO$_2$S 296.0751 [M$^-$–H], Found 296.0760.

5b: 5-bromo-3-[(4-methoxycarbonylphenyl)aminomethyl]benzothiophene 70% as brown powder; recrystallization from EtOH; m.p. 143° C.; $^1$H-NMR (300 MHz, CDCl$_3$): δ=3.86 (s, 3H); 4.48 (s(broad), 1H); 4.56 (s, 2H); 6.64 (d, J=8.5 Hz, 2H); 7.37 (s, 1H); 7.48 (d, J=8.3 Hz, 1H); 7.74 (d, J=8.3 Hz, 1H); 7.89 (d, J=8.5 Hz, 2H); 7.92 (s, 1H); $^{13}$C-NMR (75 MHz, CDCl$_3$): δ=42.1, 51.7, 111.9, 118.6, 119.3, 124.4, 124.5, 125.8, 127.9, 131.7, 132.3, 139.4, 139.6, 151.5 and 167.3; IR (cm$^{-1}$): ν=3376 (NH); 1683 (C=O); MS (70 eV): m/z (%)=374/6 (100) [M$^-$–H]; HRMS (ESI) Anal. Calcd. for C$_{17}$H$_{13}$BrNO$_2$S 373.9856 [M$^-$–H], Found 373.9869.

5c: 3-[(4-methoxycarbonylphenyl)aminomethyl]-5-phenylbenzothiophene 75% as brown powder; R$_f$ 0.29 (EtOAc/PE 1/5); m.p. 154° C.; $^1$H-NMR (300 MHz, CDCl$_3$): δ=3.85 (s, 3H); 4.49 (s(broad), 1H); 4.65 (d, J=4.9 Hz, 2H); 6.65 (d, J=8.8 Hz, 2H); 7.33-7.48, 7.62-7.65 and 7.88-7.96 (3×m, 4H, 3H and 4H); $^{13}$C-NMR (75 MHz, CDCl$_3$): δ=42.3, 51.7, 111.9, 119.1, 120.0, 123.4, 124.5, 124.9, 127.5, 127.6, 129.0, 131.7, 133.0, 138.1, 138.3, 140.0, 141.2, 151.7 and 167.3; IR (cm$^{-1}$): ν=3389 (NH); 1697 (C=O); MS (70 eV): m/z (%)=372 (25) [M$^-$–H]; HRMS (ESI) Anal. Calcd. for C$_{23}$H$_{18}$NO$_2$S 372.1064 [M$^-$–H], Found 372.1069.

5d: 3-[(4-methoxycarbonyl-2-methylphenyl)aminomethyl]benzothiophene 50% as white powder; recrystallization from EtOH; m.p. 148° C.; $^1$H-NMR (300 MHz, CDCl$_3$): δ=2.15 (s, 3H); 3.85 (s, 3H); 4.29 (s(broad), 1H); 4.64 (s, 2H); 6.66 (d, J=8.8 Hz, 1H); 7.33 (s, 1H); 7.37-7.43 and 7.78-7.89 (2×m, 2H and 4H); $^{13}$C-NMR (75 MHz, CDCl$_3$): δ=17.5, 42.4, 51.7, 108.9, 118.5, 121.2, 121.7, 123.2, 124.2, 124.5, 124.8, 129.9, 131.7, 132.8, 137.8, 141.0, 149.8 and 167.6; IR (cm$^{-1}$): ν=3442 (NH); 1702 (C=O); MS (70 eV): m/z (%)=310 (100) [M$^-$–H]; HRMS (ESI) Anal. Calcd. for C$_{18}$H$_{16}$NO$_2$S 310.0907 [M$^-$–H], Found 310.0917.

11a: 6-bromo-3-[(4-methoxycarbonylphenyl)aminomethyl]-benzothiophene 50% as light yellow powder; recrystallization from EtOH; m.p. 155° C.; $^1$H-NMR (400 MHz, [D$_6$]DMSO): δ=3.74 (s, 3H); 4.57 (d, J=5.5 Hz, 2H); 6.70 (d, J=8.8 Hz, 2H); 7.12 (t, J=5.5 Hz, 1H); 7.58 (dd, J=8.6, 1.8 Hz, 1H); 7.65 (s, 1H); 7.69 (d, J=8.8 Hz, 2H); 7.89 (d, J=8.6 Hz, 1H); 8.30 (d, J=1.8 Hz, 1H); $^{13}$C-NMR (100.6 MHz, [D$_6$]DMSO): δ=41.1, 51.7, 111.8, 116.6, 118.1, 124.2, 125.7, 125.8, 127.7, 131.4, 133.8, 137.4, 142.4, 153.0 and 166.8; IR (cm$^{-1}$): ν=3346 (NH); 1672 (C=O); MS (70 eV): m/z (%)=374/6 (20) [M$^-$–H]; HRMS (ESI) Anal. Calcd. for C$_{17}$H$_{13}$BrNO$_2$S 373.9856 [M$^-$–H], Found 373.9862.

11b: 3-[(4-methoxycarbonylphenyl)aminomethyl]-6-phenyl-benzothiophene 66% as white powder; recrystallization from EtOH; m.p. 169° C.; $^1$H-NMR (400 MHz, CDCl$_3$): δ=3.86 (s, 3H); 4.48 (t, J=5.0 Hz, 1H); 4.64 (d, J=5.0 Hz, 2H); 6.66 (d, J=8.8 Hz, 2H); 7.36-7.40 (m, 2H); 7.48 (t, J=7.6 Hz, 2H); 7.64-7.67 (m, 3H); 7.85 (d, J=8.4 Hz, 1H); 7.90 (d, J=8.8 Hz, 2H); 8.09 (d, J=1.2 Hz, 1H); $^{13}$C-NMR (100.6 MHz, CDCl$_3$): δ=42.2, 51.6, 111.7, 119.0, 121.4, 121.8, 124.1, 124.4, 127.4, 127.5, 128.9, 131.6, 132.5, 136.8, 138.2, 140.8, 141.6, 151.6 and 167.3; IR (cm$^{-1}$): ν=3390 (NH); 1683 (C=O); MS (70 eV): m/z (%)=396 (30) [M$^+$+Na].

Synthesis of Tertiary Amines 6a-c and 12a-b

The synthesis of 3-[N-benzyl-N-(4-methoxycarbonylphenyl)aminomethyl]-benzothiophene 6a will be used as an example for the synthesis of tertiary amines 6a-c and 12a-b. 3-[(4-Methoxycarbonylphenyl)aminomethyl]-benzothiophene 5a (297 mg, 1 mmol, 1 equiv) was dissolved in DMF (10 mL) and to this solution was sodium hydride (40 mg, 60% dispersion in mineral oil, 1 mmol, 1 equiv) added. The reaction mixture was stirred for 30 minutes at room temperature under nitrogen atmosphere after which benzyl bromide (342 mg, 2 mmol, 2 equiv) and potassium iodide (5 mg) were added. After two hours the reaction mixture was poured in to brine (20 mL) and three times extracted with EtOAc (20 mL). The combined organic fraction was thereafter three times washed with brine (15 mL), dried (MgSO$_4$), filtered and evaporated under vacuum. Purification through column chromatography (R$_f$ 0.30, EtOAc/PE 1/5) yielded 3-[N-benzyl-N-(4-methoxycarbonylphenyl)-aminomethyl]benzothiophene 6a (271 mg, 0.7 mmol, 70%) as a yellow powder.

6a: 3-[N-benzyl-N-(4-methoxycarbonylphenyl)aminomethyl]-benzothiophene 70% as yellow powder; R$_f$ 0.30 (EtOAc/PE 1/5); m.p. 126° C.; $^1$H-NMR (300 MHz, CDCl$_3$): δ=3.84 (s, 3H); 4.76 and 4.87 (2×s, 2×2H); 6.76 (d, J=8.8 Hz, 2H); 7.11 (s, 1H); 7.21-7.40, 7.65-7.68 and 7.85-7.90 (3×m, 7H, 1H and 3H); $^{13}$C-NMR (75 MHz, CDCl$_3$): δ=49.6, 51.7, 54.0, 111.5, 118.3, 121.3, 122.8, 123.2, 124.3, 124.8, 126.6, 127.4, 129.0, 131.4, 131.6, 137.5, 137.6, 141.3, 152.4 and 167.3; IR (cm$^{-1}$): ν=1701 (C=O); MS (70 eV): m/z (%)=388 (85) [M$^+$+H]; HRMS (ESI) Anal. Calcd. for C$_{24}$H$_{22}$NO$_2$S 388.1366 [M$^+$+H], Found 388.1374.

6b: 5-bromo-3-[N-benzyl-N-(4-methoxycarbonylphenyl)aminomethyl]-benzothiophene 79% as yellow powder; R$_f$ 0.37 (EtOAc/PE 1/5); m.p. 130° C.; $^1$H-NMR (300 MHz, CDCl$_3$): δ=3.84 (s, 3H); 4.76 and 4.87 (2×s, 2×2H); 6.76 (d, J=8.8 Hz, 2H); 7.11 (s, 1H); 7.22-7.41, 7.65-7.68 and 7.85-7.91 (3×m, 6H, 1H and 3H); $^{13}$C-NMR (75 MHz, CDCl$_3$): δ=49.4, 51.7, 54.1, 111.5, 118.5, 124.2, 124.5, 126.6, 127.5, 127.8, 129.0, 130.9, 131.6, 137.3, 139.2, 139.9, 152.2 and 167.3; IR (cm$^-$): ν=1702 (C=O); MS (70 eV): m/z (%)=466/8 (100) [M$^+$+H]; HRMS (ESI) Anal. Calcd. for C$_{24}$H$_{21}$BrNO$_2$S 466.0471 [M$^+$+H], Found 466.0483.

6c: 3-[N-benzyl-N-(4-methoxycarbonylphenyl)aminomethyl]-5-phenyl-benzothiophene 65% as yellow powder; R$_f$ 0.31 (EtOAc/PE 1/5); m.p. 82° C.; $^1$H-NMR (300 MHz, CDCl$_3$): δ=3.83 (s, 3H); 4.76 and 4.90 (2×s, 2×2H); 6.76 (d, J=8.8 Hz, 2H); 7.13 (s, 1H); 7.22-7.46, 7.59-7.63 and 7.83-7.93 (3×m, 8H, 3H and 4H); $^{13}$C-NMR (75 MHz, CDCl$_3$): δ=49.7, 51.7, 54.1, 111.6, 118.4, 119.8, 123.4, 123.5, 124.5, 126.6, 127.4, 127.5, 129.0, 131.6, 131.7, 137.5, 138.0, 138.2, 140.4, 141.2, 152.4 and 167.3; IR (cm$^{-1}$): ν=1702 (C=O); MS (70 eV): m/z (%)=464 (70)

[M⁺+H]; HRMS (ESI) Anal. Calcd. for $C_{30}H_{26}NO_2S$ 464.1679 [M⁺+H], Found 464.1698.

12a: 6-bromo-3-[N-benzyl-N-(4-methoxycarbonylphenyl)aminomethyl]-benzothiophene 87% as white powder; $R_f$ 0.21 (EtOAc/PE 1/10); m.p. 63° C.; ¹H-NMR (400 MHz, [D₆]DMSO): δ=3.74 (s, 3H); 4.83 and 5.01 (2×s, 2×2H); 6.79 (d, J=9.1 Hz, 2H); 7.24-2.28 and 7.32-7.36 (2×m, 3H and 2H); 7.38 (s, 1H); 7.58 (dd, J=8.6, 1.8 Hz, 1H); 7.71 (d, J=9.1 Hz, 2H); 7.80 (d, J=8.6 Hz, 1H); 8.31 (d, J=1.8 Hz, 1H); ¹³C-NMR (100.6 MHz, [D₆]DMSO): δ=49.7, 51.8, 54.1, 112.1, 117.1, 118.2, 124.0, 124.6, 125.9, 127.0, 127.4, 127.7, 129.1, 131.3, 132.4, 137.0, 138.5, 142.6, 152.2 and 166.6; IR (cm⁻¹): ν=1702 (C=O); MS (70 eV): m/z (%)=466/8 (100) [M⁺+H]; HRMS (ESI) Anal. Calcd. for $C_{24}H_{21}BrNO_2S$ 466.0471 [M⁺+H], Found 466.0482.

12b: 3-[N-benzyl-N-(4-methoxycarbonylphenyl)aminomethyl]-6-phenyl-benzothiophene 91% as white powder; $R_f$ 0.13 (EtOAc/PE 1/10); m.p. 66° C.; ¹H-NMR (400 MHz, CDCl₃): δ=3.84 (s, 3H); 4.76 and 4.88 (2>s, 2×2H); 6.77 (d, J=9.1 Hz, 2H); 7.11 (s, 1H); 0.7.23-7.39, 7.45-7.48, 7.61-7.66 and 7.70-7.72 (4×m, 6H, 2H, 3H and 1H); 7.87 (d, J=9.1 Hz, 2H); 8.08 (d, J=1.0 Hz, 1H); ¹³C-NMR (100.6 MHz, CDCl₃): δ=49.5, 51.6, 53.9, 111.5, 118.2, 121.4, 121.5, 123.1, 124.0, 126.5, 2×127.4, 127.5, 2×128.9, 131.2, 131.6, 136.6, 137.4, 138.1, 140.9, 142.0, 152.3 and 167.2; IR (cm⁻¹): ν=1702 (C=O); MS (70 eV): m/z (%)=464 (100) [M⁺+H]; HRMS (ESI) Anal. Calcd. for $C_{30}H_{26}NO_2S$ 464.1679 [M⁺+H], Found 464.1672.

Synthesis of 3-[(4-methoxycarbonylphenyl)iminomethyl]indole 16

Indole-3-carbaldehyde 15 (435 mg, 3 mmol, 1 equiv), methyl 4-aminobenzoate (544 mg, 3.6 mmol, 1.2 equiv) and p-toluenesulfonic acid monohydrate (29 mg, 0.15 mmol, 0.05 equiv) were added to toluene (25 mL) in a Dean Stark apparatus. After 18 hour refluxing the mixture was extracted with EtOAc (25 mL) and washed with a saturated aqueous solution of sodium bicarbonate (25 mL), water (25 mL) and brine (25 mL). Drying (MgSO₄), filtering and evaporating of the organic layer yielded a yellow crude reaction mixture which was recrystallized from EtOAc/hexane to obtain 3-[(4-methoxycarbonylphenyl)iminomethyl]indole 16 (710 mg, 2.55 mmol, 85%) as a light yellow powder.

16: 3-[(4-methoxycarbonylphenyl)iminomethyl]indole 85% as light yellow powder; recrystallization from EtOAc/hexane; m.p. 159° C.; ¹H-NMR (400 MHz, CDCl₃): δ=3.92 (s, 3H); 7.24 (d, J=8.2 Hz, 2H); 7.29-7.31 and 7.38-7.40 (2×m, 2H and 1H); 7.64 (s, 1H); 8.07 (d, J=8.2 Hz, 2H); 8.49-8.51 (m, 1H); 8.62 (s, 1H); 8.83 (s(broad), 1H); ¹³C-NMR (100.6 MHz, CDCl₃): δ=52.0, 111.4, 116.5, 120.9, 122.1, 122.3, 123.9, 125.1, 126.3, 130.9, 131.2, 136.9, 155.7, 157.7 and 167.2; IR (cm⁻¹): ν=3292 (NH); 1698 (C=O); MS (70 eV): m/z (%)=279 (100) [M⁺+H]; HRMS (ESI) Anal. Calcd. for $C_{17}H_{15}N_2O_2$ 279.1128 [M⁺+H], Found 279.1135.

Synthesis of 3-[(4-methoxycarbonylphenyl)aminomethyl]indole 17

3-[(4-Methoxycarbonylphenyl)iminomethyl]indole 16 (417 mg, 1.5 mmol, 1 equiv) was dissolved in methanol (20 mL). To this solution was sodium borohydride (284 mg, 7.5 mmol, 5 equiv) added after which the mixture was heated to its boiling point. After 90 minutes of stirring the mixture was cooled to room temperature and quenched with water. The obtained mixture was extracted with EtOAc (2×25 mL), washed with water (25 mL) and brine (25 mL), dried (MgSO₄), filtered and evaporated under vacuum. After recrystallization from EtOAc/hexane 3-[(4-methoxycarbonylphenyl)-aminomethyl]indole 17 (370 mg, 1.32 mmol, 88%) was obtained as a yellow powder.

17: 3-[(4-methoxycarbonylphenyl)aminomethyl]indole 88% as yellow powder; recrystallization from EtOAc/hexane; m.p. 115.5° C.; ¹H-NMR (400 MHz, [D₆]DMSO): δ=3.74 (s, 3H); 4.45 (d, J=5.3 Hz, 2H); 6.72 (d, J=8.8 Hz, 2H); 6.87 (t, J=5.3 Hz, 1H); 7.01 and 7.10 (2×t, J=7.5 Hz, 2×1H); 7.35-7.39 and 7.62-7.64 (2×m, 2H and 1H); 7.70 (d, J=8.8 Hz, 2H); 10.95 (s(broad), 1H); ¹³C-NMR (100.6 MHz, [D₆]DMSO): δ=38.7, 51.6, 111.6, 111.9, 112.2, 116.0, 119.0, 119.2, 121.6, 124.4, 127.1, 131.3, 136.9, 153.4 and 166.9; IR (cm⁻¹): ν=3360 (NH); 1685 (C=O); MS (70 eV): m/z (%)=279 (20) [M⁻–H]; HRMS (ESI) Anal. Calcd. for $C_{17}H_{15}N_2O_2$ 279.1139 [M⁻–H], Found 279.1146.

Synthesis of Hydroxamic Acids 7a-d, 8a-c, 13a-b, 14a-b and 18

The synthesis of 3-[(4-hydroxycarbamoylphenyl)aminomethyl]benzothiophene 7a, will be used as an example for the synthesis of hydroxamic acids 7a-d, 8a-c, 13a-b, 14a-b and 18. 3-[(4-Methoxycarbonylphenyl)aminomethyl]-benzothiophene 6a (400 mg, 1.35 mmol, 1 equiv) was dissolved in ethanol (10 mL) and to this solution was firstly hydroxylamine (8.3 mL, 50% in water, 135 mmol, 100 equiv) added and secondly potassium hydroxide (16.9 mL, 4M in methanol, 67.5 mmol, 50 equiv). The resulting mixture was stirred for an additional 10 minutes at room temperature before it was poured in a saturated aqueous solution of sodium bicarbonate (10 mL). This aqueous solution was extracted two times with ethyl acetate, after which the combined organic fractions were washed with water (10 mL) and brine (10 mL). After drying (MgSO₄), filtering and evaporating a very viscous colorless liquid was obtained which was recrystallized overnight from CHCl₃ to obtain 3-[(4-hydroxycarbamoylphenyl)aminomethyl]benzothiophene 7a (161 mg, 0.54 mmol, 40%) as a white powder. For hydroxamic acids 7b-d and 8a-c the mixture was stirred for 10 minutes in ethanol at refluxing conditions and for hydroxamic acids 13a-b, 14a-b and 18 the mixture was stirred for 10 minutes in THF at room temperature.

7a: 3-[(4-hydroxycarbamoylphenyl)aminomethyl]benzothiophene 40% as white powder; crystallization from CHCl₃; m.p. 191° C.; ¹H-NMR (300 MHz, [D₆]DMSO): δ=4.53 (d, J=5.5 Hz, 2H); 6.64 (d, J=8.6 Hz, 2H); 6.78 (t, J=5.5 Hz, 1H); 7.35-7.43 (m, 2H); 7.50 (d, J=8.6 Hz, 2H); 7.59 (s, 1H); 7.90-8.00 (m, 2H); 8.67 (s(broad), 1H); 10.76 (s(broad), 1H); ¹³C-NMR (75 MHz, [D₆]DMSO): δ=41.4, 111.7, 120.1, 122.7, 123.5, 124.5, 124.7, 125.0, 128.8, 134.5, 138.5, 140.6, 151.6, and 165.5; IR (cm⁻¹): ν=3380, 3255, 3105 (NH/OH); ν=1600 (C=O); MS (70 eV): m/z (%)=299 (100) [M⁺+H]; HRMS (ESI) Anal. Calcd. for $C_{16}H_{15}N_2O_2S$ 299.0849 [M⁺+H], Found 299.0862.

7b: 5-bromo-3-[(4-hydroxycarbamoylphenyl)aminomethyl]-benzothiophene 85% as white powder; crystallization from CHCl₃; m.p. 199° C.; ¹H-NMR (300 MHz, [D₆]DMSO): δ=4.52 (d, J=5.5 Hz, 2H); 6.64 (d, J=8.5 Hz, 2H); 6.82 (t, J=5.5 Hz, 1H); 7.50 (d, J=8.5 Hz, 2H and 1H); 7.69 (s, 1H); 7.96 (d, J=8.5 Hz, 1H); 8.17 (s, 1H); 8.67 (s(broad), 1H); 10.75 (s(broad), 1H); ¹³C-NMR (75 MHz, [D₆]DMSO): δ=41.2, 111.8, 118.2, 120.2, 125.3, 125.5, 126.7, 127.7, 128.8, 134.1, 139.6, 140.4, 151.5 and 165.5; IR (cm⁻¹): ν=3376, 3235 (NH/OH); 1604 (C=O); MS (70 eV): m/z (%)=377/9 (100) [M⁺+H]; HRMS (ESI) Anal. Calcd. for $C_{16}H_{14}BrN_2O_2S$ 376.9954 [M⁺+H], Found 376.9943.

7c: 3-[(4-hydroxycarbamoylphenyl)aminomethyl]-5-phenyl-benzothiophene 33% as white powder; crystallization from CHCl₃; m.p. 181° C.; ¹H-NMR (300 MHz, [D₆]DMSO): δ=4.62 (d, J=5.5 Hz, 2H); 6.68 (d, J=8.8 Hz, 2H);

6.87 (t, J=5.5 Hz, 1H); 7.35-7.40, 7.46-7.53 and 7.65-7.76 (3×m, 1H, 4H and 4H); 8.05 (d, J=8.8 Hz, 1H); 8.19 (s, 1H); 8.67 (s(broad), 1H); 10.76 (s(broad), 1H); $^{13}$C-NMR (75 MHz, [D$_6$]DMSO): δ=41.4, 111.8, 120.0, 120.8, 123.9, 124.1, 125.3, 127.7, 127.9, 128.8, 129.5, 134.8, 137.1, 139.2, 139.8, 140.9, 151.7 and 165.5; IR (cm$^{-1}$): ν=3403, 3202 (NH/OH); 1608 (C=O); MS (70 eV): m/z (%)=375 (100) [M$^+$+H]; HRMS (ESI) Anal. Calcd. for $C_{22}H_{19}N_2O_2S$ 375.1162 [M$^+$+H], Found 375.1171.

7d: 3-[(4-hydroxycarbamoyl-2-methylphenyl)aminomethyl]-benzothiophene 40% as white powder; crystallization from CHCl$_3$; m.p. 190° C.; $^1$H-NMR (300 MHz, [D$_6$]-DMSO): δ=2.16 (s, 3H); 4.63 (d, J=5.5 Hz, 2H); 6.17 (t, J=5.5 Hz, 1H); 6.51 (d, J=8.2 Hz, 1H); 7.36-7.43 (m, 4H); 7.51 (s, 1H); 7.96 (d, J=7.7 Hz, 1H); 8.05 (d, J=7.7 Hz, 1H); 8.66 (s(broad), 1H); 10,73 (s(broad), 1H); $^{13}$C-NMR (75 MHz, [D$_6$]-DMSO): δ=18.5, 41.7, 109.0, 119.9, 121.6, 122.7, 123.5, 124.1, 124.6, 125.0, 126.5, 129.4, 134.7, 138.4, 140.7, 149.2 and 165.6; IR (cm$^{-1}$): ν=3396, 3366, 3260 (NH/OH); ν=1604 (C=O); MS (70 eV): m/z (%)=313 (100) [M$^+$+H]; HRMS (ESI) Anal. Calcd. for $C_{17}H_{17}N_2O_2S$ 313.1005 [M$^+$+H], Found 313.1019.

8a: 3-[N-benzyl-N-(4-hydroxycarbamoylphenyl)aminomethyl]-benzothiophene 17% as brown powder; R$_f$ 0.14 (CH$_2$Cl$_2$/MeOH/Et$_3$N 95/5/2); m.p. 178° C.; $^1$H-NMR (300 MHz, CDCl$_3$): δ=4.74 and 4.85 (2×s, 2×2H); 6.74-6.76 (m, 2H); 7.09 (s, 1H); 7.20-7.40, 7.57-7.67 and 7.87-7.90 (3×m, 7H, 3H and 1H); $^{13}$C-NMR (75 MHz, CDCl$_3$): δ=49.5, 54.0, 111.9, 118.6, 121.4, 122.8, 123.2, 124.3, 124.8, 126.6, 127.4, 128.8, 128.9, 131.4, 137.5, 137.6, 141.3, 151.8 and 167.4; IR (cm$^{-1}$): ν=3059 (NH/OH); 1604 (C=O); MS (70 eV): m/z (%)=389 (100) [M$^+$+H]; HRMS (ESI) Anal. Calcd. for $C_{23}H_{21}N_2O_2S$ 389.1318 [M$^+$+H], Found 389.1334.

8b: 5-bromo-3-[N-benzyl-N-(4-hydroxycarbamoylphenyl)aminomethyl]-benzothiophene 13% as a white powder; R$_f$ 0.14 (CH$_2$Cl$_2$/MeOH/Et$_3$N 95/5/2); m.p. 179° C.; $^1$H-NMR (300 MHz, [D$_6$]acetone): δ=4.84 and 5.03 (2×s, 2×2H); 6.82 (d, J=8.8 Hz, 2H); 7.24-7.37 (m, 6H); 7.53 (d, J=8.8 Hz, 1H); 7.66 (d, J=8.8 Hz, 2H); 7.93 (d, J=8.8 Hz, 1H); 8.05 (s, 1H); 10.45 (s(broad), 1H); $^{13}$C-NMR (75 MHz, [D$_6$]acetone): δ=49.6, 54.1, 111.9, 117.9, 119.7, 124.7, 124.8, 126.7, 127.0, 127.5, 128.4, 128.7, 132.2, 138.5, 139.8, 140.0, 151.2 and 165.7; IR (cm$^{-1}$): ν=3199 (NH/OH); 1605 (C=O); MS (70 eV): m/z (%)=465/7 (22) [M$^-$−H]; HRMS (ESI) Anal. Calcd. for $C_{23}H_{18}BrN_2O_2S$ 465.0278 [M$^-$−H], Found 465.0287.

8c: 3-[N-benzyl-N-(4-hydroxycarbamoylphenyl)aminomethyl]-5-phenyl-benzothiophene 13% as yellow powder; R$_f$ 0.14 (CH$_2$Cl$_2$/MeOH/Et$_3$N 95/5/2); m.p. 126° C.; $^1$H-NMR (300 MHz, CDCl$_3$): δ=4.73 and 4.88 (2×s, 2×2H); 6.73-3.79 (m, 2H); 7.11-7.46 and 7.59-7.63 (2×m, 10H and 4H); 7.81 (s, 1H); 7.92 (d, J=8.3 Hz, 1H); 8.63 (s(broad), 1H); $^{13}$C-NMR (75 MHz, CDCl$_3$): δ=49.7, 54.0, 112.0, 118.4, 119.8, 123.4, 123.5, 124.4, 126.6, 127.4, 127.5, 128.8, 129.0, 131.5, 137.4, 137.9, 138.1, 140.3, 141.1, 152.0 and 167.6. IR (cm$^{-1}$): ν=3198 (NH/OH); 1604 (C=O); MS (70 eV): m/z (%)=465 (100) [M$^+$+H]; HRMS (ESI) Anal. Calcd. for $C_{29}H_{25}N_2O_2S$ 465.1631 [M$^+$+H], Found 465.1639.

13a: 6-bromo-3-[(4-hydroxycarbamoylphenyl)aminomethyl]-benzothiophene 80% as white powder; crystallization from CHCl$_3$; m.p. 179.5° C.; $^1$H-NMR (400 MHz, [D$_6$] DMSO): δ=4.54 (d, J=5.5 Hz, 2H); 6.65 (d, J=8.6 Hz, 2H); 6.80 (t, J=5.5 Hz, 1H); 7.52 (d, J=8.6 Hz, 2H); 7.58 (dd, J=8.6, 1.7 Hz, 1H); 7.64 (s, 1H); 7.90 (d, J=8.6 Hz, 1H); 8.30 (d, J=1.6 Hz, 1H); 8.69 (s(broad), 1H); 10.78 (s(broad), 1H); $^{13}$C-NMR (100.6 MHz, [D$_6$]-DMSO): δ=41.2, 111.6, 118.0, 120.0, 124.2, 125.5, 125.8, 127.6, 128.7, 134.2, 137.4, 142.4, 151.5 and 165.3; IR (cm$^{-1}$): ν=3417, 3220 (NH/OH); 1604 (C=O); MS (70 eV): m/z (%)=375/7 (100) [M$^-$−H]; HRMS (ESI) Anal. Calcd. for $C_{16}H_{12}BrN_2O_2S$ 374.9808 [M$^-$−H], Found 374.9815.

13b: 3-[(4-hydroxycarbamoylphenyl)aminomethyl]-6-phenyl-benzothiophene 68% as white powder; crystallization from CHCl$_3$; m.p. 190.5° C.; $^1$H-NMR (400 MHz, [D$_6$]DMSO): δ=4.58 (d, J=5.6 Hz, 2H); 6.68 (d, J=8.8 Hz, 2H); 6.82 (t, J=5.6 Hz, 1H); 7.39 (t, J=7.3 Hz, 1H); 7.48-7.55 (m, 4H); 7.64 (s, 1H); 7.72-7.78 (m, 3H); 8.03 (d, J=8.4 Hz , 1H); 8.67 (s(broad), 1H); 10.77 (s(broad), 1H); $^{13}$C-NMR (100.6 MHz, [D$_6$]DMSO): δ=41.4, 111.7, 120.0, 121.3, 123.0, 123.7, 125.0, 127.4, 127.9, 128.7, 129.5, 134.2, 137.1, 137.7, 140.5, 141.5, 151.5 and 165.4; IR (cm$^{-1}$): ν=3411, 3254 (NH/OH); 1604 (C=O); MS (70 eV): m/z (%)=375 (35) [M$^+$+H]; HRMS (ESI) Anal. Calcd. for $C_{22}H_{19}N_2O_2S$ 375.1162 [M$^+$+H], Found 375.1154.

14a: 6-bromo-3-[N-benzyl-N-(4-hydroxycarbamoylphenyl)aminomethyl]-benzothiophene 56% as light brown powder; recrystallization from CHCl$_3$/ether; m.p. 97.5° C.; $^1$H-NMR (400 MHz, CDCl$_3$): δ=4.73 and 4.83 (2×s, 2×2H); 6.76 (d, J=8.2 Hz, 2H); 7.08 (s, 1H); 7.21 (d, J=7.1 Hz, 2H); 7.29-7.36 (m, 3H); 7.50 (s, 2H); 7.59 (d, J=8.2 Hz, 2H); 8.02 (s, 1H); $^{13}$C-NMR (100.6 MHz, CDCl$_3$): δ=49.3, 53.9, 111.9, 118.2, 118.8, 122.3, 123.2, 125.6, 126.4, 127.4, 127.7, 128.7, 128.9, 131.1, 136.2, 137.1, 142.6, 151.8 and 167.6; IR (cm$^{-1}$): ν=3061 (NH/OH); 1602 (C=O); MS (70 eV): m/z (%)=467/9 (100) [M$^+$+H]; HRMS (ESI) Anal. Calcd. for $C_{23}H_{18}BrN_2O_2S$ 467.0423 [M$^+$+H], Found 467.0423.

14b: 3-[N-benzyl-N-(4-hydroxycarbamoylphenyl)aminomethyl]-6-phenyl-benzothiophene 74% as white powder; recrystallization from CHCl$_3$/ether; m.p. 102° C.; $^1$H-NMR (400 MHz, [D$_6$]DMSO): δ=4.82 and 5.02 (2×s, 2×2H); 6.75 (d, J=9.0 Hz, 2H); 7.24-7.41 (m, 7H); 7.50 (t, J=7.6 Hz, 2H); 7.55 (d, J=9.0 Hz, 2H); 7.74 (dd, J=8.4, 1.6 Hz, 1H); 7.77 (d, J=7.3 Hz, 2H); 7.94 (d, J=8.4 Hz, 1H); 8.33 (s, 1H); 8.76 (s(broad), 1H); 10.82 (s(broad), 1H); $^{13}$C-NMR (100.6 MHz, [D$_6$]DMSO): δ=49.9, 54.1, 112.0, 120.4, 121.4, 122.8, 123.8, 124.1, 127.0, 127.3, 127.4, 127.9, 128.7, 129.0, 129.5, 132.8, 137.2, 137.3, 139.0, 140.4, 141.7, 150.7 and 165.1; IR (cm$^{-1}$): ν=3026 (NH/OH); 1602 (C=O); MS (70 eV): m/z (%)=465 (100) [M$^+$+H]; HRMS (ESI) Anal. Calcd. for $C_{29}H_{25}N_2O_2S$ 465.1631 [M$^+$+H], Found 465.1640.

18: 3-[(4-hydroxycarbamoylphenyl)aminomethyl]indole 77% as yellow powder; crystallization from CHCl$_3$; m.p. 132.5° C.; $^1$H-NMR (400 MHz, [D$_6$]DMSO): δ=4.40 (d, J=5.3 Hz, 2H); 6.52 (t, J=5.3 Hz, 1H); 6.66 (d, J=8.8 Hz, 2H); 6.97-7.01, 7.06-7.10 and 7.33-7.37 (3×m, 1H, 1H and 2H); 7.51 (d, J=8.8 Hz, 2H); 7.62 (d, J=7.8 Hz, 1H); 8.66, 10.74 and 10.93 (3×s(broad), 3×1H); $^{13}$C-NMR (100.6 MHz, [D$_6$]DMSO): δ=38.8, 111.5, 111.9, 112.5, 118.9, 119.2, 119.4, 121.6, 124.3, 127.1, 128.6, 136.8, 151.8 and 165.5; IR (cm$^{-1}$): ν=3407 (NH/OH); 1601 (C=O); MS (70 eV): m/z (%)=282 (20) [M$^+$+H]; HRMS (ESI) Anal. Calcd. for $C_{16}H_{16}N_3O_2$ 282.1237 [M$^+$+H], Found 282.1236.

Ligand Docking

All manipulations were performed with the molecular modelling program YASARA and the YASARA/WHATIF twinset.[16,17] The HDAC6 sequence was obtained from the UniProt database (www.uniprot.org; UniProt entry Q9UBN7). To increase the accuracy of the model, the sequence was limited to the major functional domain of HDAC6 (Gly482-Gly800). Possible templates were identified by running 3 PSI-BLAST iterations to extract a position specific scoring matrix (PSSM) from UniRef90, and then searching the PDB for a match. To aid the alignment of the HDAC6 sequence and templates, and the modelling of the loops, a secondary structure prediction was performed, followed by multiple sequence alignments. All side chains were ionised or kept neutral according to their predicted pKa values. Initial models were created from different templates, each with several alignment variations and up to hundred conformations tried per loop. After the side-chains had been built, optimised and fine-tuned, all newly modelled parts were subjected to a combined steepest descent and simulated annealing minimisation, i.e. the backbone atoms of aligned residues were kept fixed to preserve the folding, followed by a full unrestrained simulated annealing minimisation for the entire model. The final model was obtained as a hybrid model of the best parts of the initial models, and checked once more for anomalies like incorrect configurations or colliding side chains. Furthermore, it was structurally aligned with known HDAC crystal structures to check if the chelating residues and the zinc atom were arranged correctly.

The HDAC inhibitor structures were created with YAS-ARA Structure1 and energy minimised with the AMBER03 force field.[18] The grid box used for docking had a dimension of 25×25×25 angstrom with a grid spacing of 0.2 Å, and comprised the entire catalytic cavity including the Zn ion and the outer surface of the active site entrance. Docking was performed with AutoDock 4.2[19] using the AMBER03 force field and default parameters. Ligands were allowed to freely rotate during docking. The figure (not shown) was created with PyMol v1.3.[20]

Cell Culture Western Blot

Mouse neuroblastoma (Neuro-2a) cells were grown in a 1:1 mix of D-MEM (Dulbecco's Modified Eagle Medium) and F12 medium supplemented with glutamax (Invitrogen), 100 µg/ml streptomycin, 100 U/ml penicillin (Invitrogen), 10% fetal calf serum (Greiner Bio-one), 1% non-essential amino acids (Invitrogen) and 1.6% NaHCO$_3$ (Invitrogen) at 37° C. and 7.5% CO$_2$. To split the cells, cells were washed with Versene (Invitrogen) and dissociated with 0.05% Trypsine-EDTA (Invitrogen). The Neuro-2a cells were treated overnight at 37° C. with dosages ranging from 10 nM up to 1 µM of either Tubastatin A (Sigma-Aldrich) or the candidate HDAC6 inhibitors.

Western Blot

For sodium dodecyl sulfate-polyacrylamide gel electrophoresis (SDS-PAGE) analysis, transfected cells were collected using the EpiQuik Total Histone Extraction Kit (Epi-Gentek) according to manufacturer's instructions. Protein concentrations were determined using microBCA kit (Thermo Fisher Scientific Inc., Pittsburgh, Pa., USA) according to manufacturer's instructions. Before resolving the samples on a 12% SDS-PAGE gel, samples containing equal amounts of protein were supplemented with reducing sample buffer (Thermo Scientific) and boiled at 95° C. for 5 min. After electrophoresis, the proteins were transferred to a polyvinylidene difluoride (PVDF) membrane (Millipore Corp., Bedford, Mass., USA). The non-specific binding was blocked by incubation of the membrane in 5% bovine serum albumin (BSA), diluted in Tris Buffered Saline Tween (TBST, 50 mM TRIS, 150 mM NaCl, 0.1% Tween-20 (Applichem, Darmstadt, Duitsland) for 1 h at room temperature followed by incubation with primary antibodies overnight. The antibodies, diluted in TBS-T, were directed against α-tubulin (1/5000, T6199, Sigma-Aldrich), and acetylated α-tubulin (1/5000, T6793 monoclonal, Sigma-Aldrich). The secondary antibodies, coupled to alkaline phosphatase (anti-mouse or anti-rabbit, 1/5000, Sigma-Aldrich) were used. Blots were visualised by adding the ECF substrate (Enhanced Chemical Fluorescence, GE Healthcare, Uppsala, Sweden) and imaged with the ImageQuant_LAS 4000. A mild reblotting buffer (Millipore) was applied to strip the blots. ImageQuant TL version 7.0-software was used to quantify the blots.

Results

In vitro pharmacological studies of novel hydroxamic acids 7a-d, 8a-c, 13a-b, 14a-b and 15 with regard to their HDAC6 inhibitory activity revealed interesting SAR information (Table 1). The mother structure 7a, bearing no substituents, and bromo-substituted compounds 7b and 13a were identified as the most potent HDAC6 inhibitors. Surprisingly, and in contrast with the predicted binding mode, N-benzylation of secondary amines drastically reduced the inhibitory activity; the same holds for the introduction of a phenyl group on the benzothiophene ring. Decoration of the benzene linker with a methyl group also resulted in loss of HDAC6 inhibitor activity. The indole-containing hydroxamic acid 18 showed promising HDAC6 inhibitor activity with an IC$_{50}$-value of 0.2 µM, albeit considerably less as compared to its benzothiophene counterpart 7a (IC$_{50}$=0.014 µM). This observation corroborates the hypothesis of a presumed higher affinity of the more hydrophobic benzothiophene scaffold as compared to the indole system.

TABLE 1

In vitro pharmacological data: HDAC6 inhibition[a]

| Compound | R$^1$ | R$^2$ | % Inhibition (10 µM) | IC$_{50}$ (µM) |
|---|---|---|---|---|
| 7a | H | H | 99.8 | 0.014 |
| 7b | Br | H | 99.2 | 0.037 |
| 7c | Ph | H | 95.1 | 0.31 |
| 7d | H | Me | 73.4 | 2.4 |
| 8a | H | — | 89.9 | 0.47 |
| 8b | Br | — | 84.9 | 0.85 |
| 8c | Ph | — | 47.9 | N.D.[b] |
| 13a | Br | — | 99.3 | 0.064 |
| 13b | Ph | — | 89.8 | 0.66 |
| 14a | Br | — | 70.7 | 2.1 |
| 14b | Ph | — | 61.1 | N.D.[b] |
| 18 | — | — | 99.0 | 0.2 |

[a]Reference compound: Trichostatin A (IC$_{50}$ = 0.014 µM)
[b]Not Determined (<70% inhibition at 10 µM)

The selectivity of the most potent HDAC6 inhibitors 7a, 7b and 13a was assessed through screening of their affinity toward all zinc-containing HDAC isozymes (Table 2). These results reveal an explicit selectivity profile for all three molecules taking their low nanomolar HDAC6 IC$_{50}$-values (<100 nM) and micromolar IC$_{50}$-values for all other HDAC isozymes into account. The least-pronounced selectivity is observed toward HDAC8 (30-100-fold selectivities) which is in line with the activity of other HDAC6 inhibitors.[13] Overall, compound 7b can be identified as an inhibitor with a very high selectivity profile for HDAC6, since this compound shows less than 50% effect at 100 µM for HDACs 1-5, 7 and 9, has IC$_{50}$-values of 33 µM and 15 µM for HDAC10 and 11 respectively and is 57-times more selective over HDAC8. This indicates that substitution on the 5-position of the benzothiophene core with a bromine atom is more beneficial to obtain a very selective HDAC6 inhibitor than substitution on the 6-position or no substitution at all. Besides these good preliminary in vitro pharmacological data, these compounds were made in only two or three steps and comply with 'Lipinski's rule of five' and thus represent useful molecules for further elaboration.

TABLE 2

In vitro pharmacological data; $IC_{50}$-values of 7a, 7b and 13a towards all HDAC isozymes (μM)[a]

| Compound | HDAC1 | HDAC2 | HDAC3 | HDAC4 | HDAC5 |
|---|---|---|---|---|---|
| 7a | 7.5 | 30 | 10 | 10 | 17 |
| 7b | >10 | N.C. | >10 | N.C. | N.C. |
| 13a | 3.4 | 20 | 6.6 | 31 | 45 |

| Compound | HDAC6 | HDAC7 | HDAC8 | HDAC9 | HDAC10 | HDAC11 |
|---|---|---|---|---|---|---|
| 7a | 0.014 | 5.2 | 1.4 | 7.1 | 9.9 | 31 |
| 7b | 0.037 | >10 | 2.1 | N.C. | 33 | 15 |
| 13a | 0.064 | 12 | 1.9 | 25 | 7.6 | 1.2 |

[a]Reference compound: Trichostatin A
N.C.: $IC_{50}$ value not calculable. Concentration-response curve shows less than 25% effect at the highest validated testing concentration (100 μM).
>Conc.: $IC_{50}$ value above the highest test concentration. Concentration-response curve shows less than 50% effect at the highest validated testing concentration (100 μM).

In a following stage, the ability of the most potent HDAC6 inhibitors 7a, 7b and 13a to modify the acetylation level of α-tubulin in Neuro-2a cells was compared with Tubastatin A, a known HDAC6-selective inhibitor. Neuro-2a cells were treated overnight with different concentrations of the HDAC6 inhibitors and the effect on the acetylation level of α-tubulin was determined using Western blots (FIG. 1). Values represent the normalized ratio Acetyl α-Tubulin/α-Tubulin against Tubastatin A (Tub A) in an established neuronal cell line (Neuro-2a cells: ATCC No CCL-131). Compound 7a, Tubastatin A proving that the compounds inhibit the deacetylation of acetylated α-tubulin in a more complex cellular environment.

Figure 2:
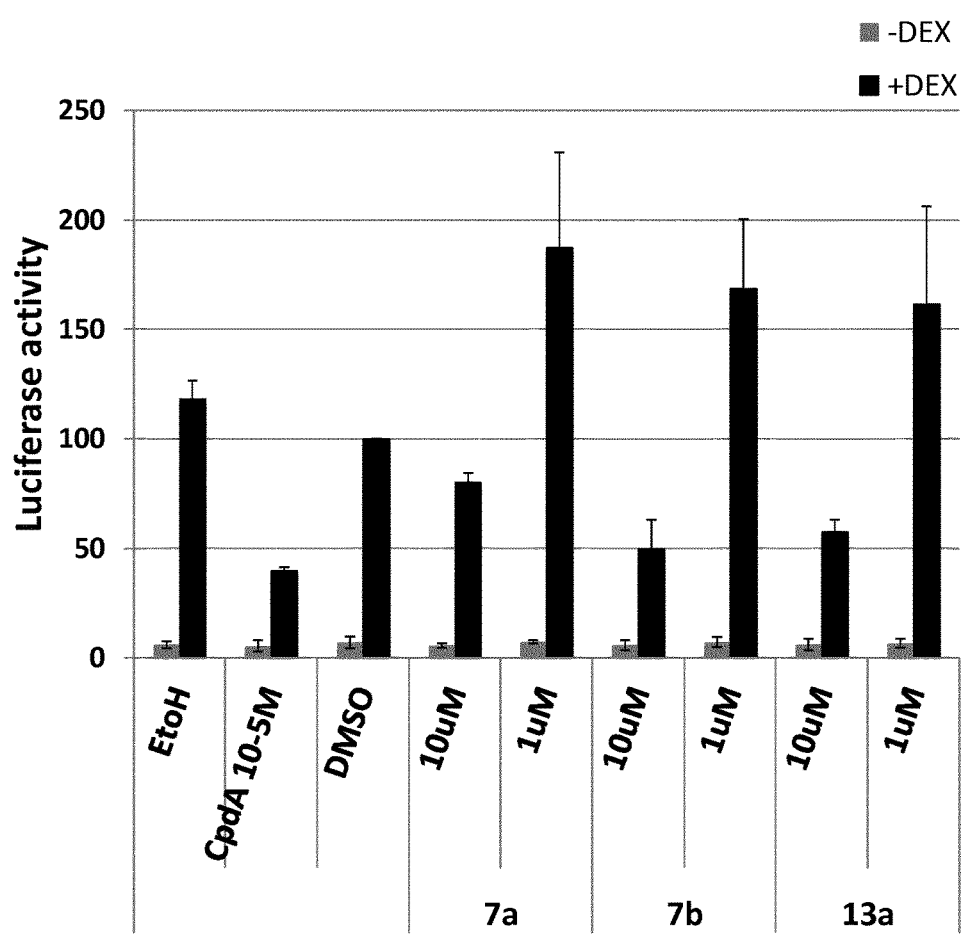
FIG. 2: A549 cells with the stably integrated recombinant reporter gene p(GRE)2-50-luc (A) were pre-incubated with respective solvents, the selective Glucocorticoid Receptor modulator CpdA (10 µM), 7a, (1 µM or 10 µM), 7b (1 µM or 10 µM), 13a (1 µM or 10 µM) for 1 h after which the synthetic glucocorticoid dexamethasone (DEX,1 µM) was added, where indicated, for 5 h. A549 cells with the stably integrated recombinant reporter gene p(IL6kB)350hu.IL6P-luc (B) or Collagenase-luc (C) were pre-incubated with respective solvents, DEX (1 µM), CpdA (10 µM), 7a, (1 µM or 10 µM), 7b (1 µM or 10 µM), 13a (1 µM or 10 µM) for 1 h after which TNF (2000 units/ml) or PMA (20 nM) were added, where indicated, for 5 h. Cell lysates were assayed for luciferase activities. Promoter activities are expressed as relative induction factor calculated as percentage of maximal DEX (A), TNF (B) or PMA (C) responses. Averaged results of three independent experiments are shown ±SD. **$p<0.0001$; *$p<0.001$; **$p<0.01$; *$p<0.05$. Assays were performed in triplicate, and results are averages of at least three independent experiments and shown ±S.D. **$p<0.0001$; *$p<0.001$; **$p<0.01$; *$p<0.05$. Statistical significance was determined on the averaged results, and analysis performed using one-way ANOVA tests followed by a Tukey multiple comparison post test.

HDAC6 is known to regulate Hsp90 acetylation and consequently also controls the chaperone-dependent activation of the glucocorticoid receptor, GR.[21] Concomitantly, in HDAC6-deficient cells, the transcriptional activation of GR is compromised. To study whether compounds 7a, 7b and 13a exhibit a direct effect on the transcriptional activity of GR, we used a glucocorticoid response element-dependent promoter fragment coupled to luciferase, stably integrated in A549 cells. As expected, the strong GR agonist dexamethasone (DEX), is able to activate the reporter gene (FIG. 2A). In accord with previous findings, the selective GR modulator compound A (CpdA),[22] which does not support transactivation, is able to partially compete with DEX and as such able to lower the GRE-dependent reporter gene activity. Remarkably, none of the HDAC6-inhibiting compounds were able to significantly inhibit DEX-activated GR-driven gene expression, albeit at the higher doses a trend towards an inhibition of promoter activity could be noted. In contrast, compound 7a, at 1 μM, was able to significantly enhance GR-driven gene expression and a similar trend could again be noted for the other two compounds at the same concentration. These results indicate that compounds 7a, 7b and 13a are able to inhibit HDAC6 at a concentration that leaves the transcriptional activity of GR unhampered.

With regard to inflammatory responses, the HDAC6 inhibitor Tubastatin A has been reported to significantly inhibit TNF-α and IL-6 in LPS stimulated human THP-1 macrophages.[23] Therefore, we addressed whether com-

|  | DMSO | Tub A 10 nM | Tub A 50 nM | Tub A 100 nM | Tub A 500 nM | Tub A 1 μM | DMSO | 7a 10 nM | 7a 50 nM | 7a 100 nM | 7a 500 nM | 7a 1 μM |
|---|---|---|---|---|---|---|---|---|---|---|---|---|
| N = 1 | 14.23 | 83.86 | 36.39 | 45.55 | 59.89 | 100.00 | 28.03 | 71.28 | 125.02 | 165.81 | 302.05 | 27.25 |
| N = 2 | 2.66 | 10.75 | 34.60 | 49.66 | 53.59 | 100.00 | 0.27 | 0.32 | 3.46 | 11.57 | 95.17 | 86.25 |
| N = 3 | 8.30 | 4.96 | 44.96 | 41.30 | 79.01 | 100.00 | 5.88 | 12.65 | 21.17 | 27.16 | 42.76 | 61.02 |
| N = 4 | 5.02 | 9.20 | 23.91 | 39.48 | 72.46 | 100.00 | 10.86 | 11.83 | 37.17 | 65.07 | 116.96 | 187.26 |
| Average | 7.55 | 27.19 | 34.97 | 44.00 | 66.24 | 100.00 | 11.26 | 24.02 | 46.70 | 67.40 | 139.23 | 90.45 |

Compound 7b

|  | DMSO | Tub A 10 nM | Tub A 50 nM | Tub A 100 nM | Tub A 500 nM | Tub A 1 μM | DMSO | 7b 10 nM | 7b 50 nM | 7b 100 nM | 7b 500 nM | 7b 1 μM |
|---|---|---|---|---|---|---|---|---|---|---|---|---|
| N = 1 | 9.04 | 15.47 | 32.35 | 47.79 | 67.73 | 100.00 | 9.72 | 17.56 | 24.55 | 36.05 | 85.99 | 99.53 |
| N = 2 | 5.31 | 2.70 | 13.55 | 31.44 | 55.71 | 100.00 | 1.31 | 1.78 | 5.36 | 7.24 | 34.97 | 83.22 |
| N = 3 | 1.95 | 4.28 | 24.46 | 29.63 | 73.97 | 100.00 | 3.87 | 3.74 | 14.84 | 23.85 | 61.59 | 69.97 |
| N = 4 | 7.25 | 12.67 | 30.11 | 56.84 | 95.18 | 100.00 | 9.30 | 10.34 | 18.25 | 41.80 | 72.25 | 80.03 |
| Average | 5.89 | 8.78 | 25.12 | 41.43 | 73.15 | 100.00 | 6.05 | 8.35 | 15.75 | 27.24 | 63.70 | 83.19 |

Compound 13a

|  | DMSO | Tub A 10 nM | Tub A 50 nM | Tub A 100 nM | Tub A 500 nM | Tub A 1 μM | DMSO | 13a 10 nM | 13a 50 nM | 13a 100 nM | 13a 500 nM | 13a 1 μM |
|---|---|---|---|---|---|---|---|---|---|---|---|---|
| N = 1 | 4.71 | 8.42 | 22.76 | 31.46 | 56.60 | 100.00 | 6.81 | 15.09 | 22.81 | 27.19 | 62.72 | 52.31 |
| N = 2 | 6.04 | 2.13 | 3.52 | 10.65 | 41.12 | 100.00 | 2.28 | 1.36 | 3.33 | 7.80 | 45.50 | 36.45 |
| N = 3 | 4.01 | 5.26 | 36.54 | 40.93 | 86.74 | 100.00 | 4.58 | 6.21 | 9.02 | 19.35 | 74.04 | 131.29 |
| N = 4 | 6.57 | 11.55 | 32.61 | 53.68 | 96.97 | 100.00 | 10.11 | 10.74 | 20.54 | 38.48 | 97.60 | 101.71 |
| Average | 5.33 | 6.84 | 23.86 | 34.18 | 70.36 | 100.00 | 5.95 | 8.35 | 13.93 | 23.21 | 69.97 | 80.44 |

These results show that compounds 7a, 7b and 13a have the same effect on the acetylation level of α-tubulin as pounds 7a, 7b and 13a are able to interfere with the activity of pro-inflammatory transcription factors, NF-κβ and AP-1

(FIGS. 2B and C). As NF-κβ was identified before as the main key transcription factor driving IL-6,[24] we investigated first whether the hydroxamic acid HDAC6 inhibitors may directly target this pro-inflammatory transcription factor. To this end, we used a recombinant reporter gene assay, consisting of three NF-κβ-responsive elements derived from the human IL-6 promoter coupled to a 50 bp TATA box of the human IL-6 promoter and a luciferase reporter.[25] As such, the anti-inflammatory effect of compounds 7a, 7b and 13a was addressed on TNF-activated A549 cells stably transfected with the NF-κβ-dependent recombinant promoter construct (p(IL6_kappaB)3-50hu.IL6Pluc). Dexamethasone (DEX) and compound A (CpdA) were again used as reference compounds for their known effect to block the activity of NF-κβ activation following activation of the glucocorticoid receptor. Surprisingly and in contrast to the reference compounds DEX and CpdA, 7a, 7b and 13a were not able to block the activity of NF-κβ and by extension, did not show any anti-inflammatory activity, at least at the transcriptional level. Since besides NF-κβ, both the IL-6 and TNFα promoters also contain response elements for the transcription factor AP-1, we decided to also test whether the compounds could target this transcription factor instead, potentially explaining the previously reported inhibitory effect of HDAC6 inhibitors on cytokine production. On the AP1-dependent luciferase reporter gene construct, pCollagenase-luc, treatment with the AP-1 activating phorbol ester PMA (phorbol 12-myristate 13-acetate) resulted in enhanced promoter activity, as expected. It was published before that CpdA does not target AP-1-driven promoters, in contrast to DEX. None of the hydroxamic acid HDAC6 inhibitors were able to repress the AP-1-driven reporter gene. On the contrary, compounds 7b and 13a, both at 10 μM, clearly induced the AP1-dependent promoter activity as compared to solvent control (DMSO). Our results indicate that HDAC6 inhibition by the hydroxamic structures targets neither NF-κβ nor AP-1 in a direct manner, i.e. at the transcriptional level.

Overall, our results demonstrate that a potent HDAC6 inhibition can be uncoupled from transcriptional inhibition at the level of activated NF-κβ, AP-1, and GR.

In summary, novel 3-[(4-hydroxycarbamoylphenyl)aminomethyl]-benzothiophenes were prepared, leading to the identification of potent HDAC6 inhibitors with an activity/selectivity profile comparable to that of Tubastatin A. Adding additional aromatic substituents decreased the affinity for HDAC6, this in contrast to what was expected from docking studies using an HDAC6 homology model. The three best HDAC6 inhibitors performed well at α-tubulin acetylation, demonstrated that HDAC6 inhibition can be uncoupled from transcriptional inhibition at the level of activated NF-κβ, AP-1, and GR, and thus can be considered as valuable new structures for elaborate research on therapeutic applications of HDAC6 inhibitors.

REFERENCES

[1] Selected reviews: (a) Dokmanovic, M.; Clarke, C.; Marks, P. A. Histone Deacetylase Inhibitors: Overview and Perspectives. *Mol. Cancer Res.* 2007, 5, 981-989. (b) Marks, P. A. Histone deacetylase inhibitors: A chemical genetics approach to understanding cellular functions. *BBA-Gene Regul. Mech.* 2010, 1799, 717-725. (c) Kim, H. J.; Bae, S. C. Histone deacetylase inhibitors: molecular mechanisms of action and clinical trials as anti-cancer drugs. *Am. J. Transl. Res.* 2011, 3, 166-179.

[2] Selected reviews: (a) Bolden, J. E.; Peart, M. J.; Johnstone, R. W. Anticancer activities of histone deacetylase inhibitors. *Nat. Rev. Drug Discov.* 2006, 5, 769-784. (b) Marcotullio, L. D.; Canettieri, G.; Infante, P.; Greco, A.; Gulino, A. Protected from the inside: Endogenous histone deacetylase inhibitors and the road to cancer. *Biochim. Biophys. Acta* 2011, 1815, 241-252. (c) Shein, N. A.; Shohami, E. Histone Deacetylase Inhibitors as Therapeutic Agents for Acute Central Nervous System Injuries. *Mol. Med.* 2011, 17, 448-456. (d) Kazantsev, A. G.; Thompson M. L. Therapeutic application of histone deacetylase inhibitors for central nervous system disorders. *Nat. Rev. Drug Discov.* 2008, 7, 854-868.

[3] De Ruijter, A. J. M.; Van Gennip, A. H.; Caron, H. N.; Kemp, S.; Van Kuilenburg, A. B. P. Histone deacetylases (HDACs): characterization of the classical HDAC family. *Biochem. J.* 2003, 370, 737-749.

[4] Karagiannis, T. C.; El-Osta, A. Will broad-spectrum histone deacetylase inhibitors be superseded by more specific compounds? *Leukemia* 2007, 21, 61-65.

[5] Thaler, F.; Minucci, S. Next generation histone deacetylase inhibitors: the answer to the search for optimized epigenetic therapies? *Expert Opin. Drug Discov.* 2011, 6, 393-404.

[6] (a) d'Ydewalle, C.; Bogaert, E.; Van Den Bosch, L. HDAC6 at the Intersection of Neuroprotection and Neurodegeneration. *Traffic* 2012, 13, 771-779. (b) Li, G.; Jiang, H.; Chang, M.; Xie, H.; Hu, L. HDAC6 α-tubulin deacetylase: A potential therapeutic target in neurodegenerative diseases. *J. Neurol. Sci.* 2011, 304, 1-8. (c) Aldana-Masangkay, G. I.; Sakamoto, K. M. The Role of HDAC6 in Cancer. *J. Biomed. Biotechnol.* 2011, 1-10. (d) Valenzuela-Fernández, A.; Cabrero, J. R.; Serrador, J. M.; Sánchez-Madrid, F. HDAC6:a key regulator of cytoskeleton, cell migration and cell-cell interactions. *Trends Cell Biol.* 2008, 18, 291-297. (e) Boyault, C.; Sadoul, K.; Pabion, M.; Khochbin, S. HDAC6, at the crossroads between cytoskeleton and cell signaling by acetylation and ubiquitination. *Oncogene* 2007, 26, 5468-5476.

[7] (a) Kalin, J. H.; Zhang, H.; Gaudrel-Grosay, S.; Vistoli, G.; Kozikowski A. P. Chiral Mercaptoacetamides Display Enantioselective Inhibition of Histone Deacetylase 6 and Exhibit Neuroprotection in Cortical Neuron Models of Oxidative Stress. *Chem. Med. Chem.* 2012, 7, 425-439. (b) Suzuki, T.; Kouketsu, A.; Itoh, Y.; Hisakawa, S.; Maeda, S.; Yoshida, M.; Nakagawa, H.; Miyata, N. Highly Potent and Selective Histone Deacetylase 6 Inhibitors Designed Based on a Small-Molecular Substrate. *J. Med. Chem.*, 2006, 49, 4809-4812. (c) Ontoria, J. M.; Altamura, S.; Di Marco, A.; Ferrigno, F.; Laufer, R.; Muraglia, E.; Palumbi, M. C.; Rowley, M.; Scarpelli, R.; Schultz-Fademrecht, C.; Serafini, S.; Steinkühler, C.; Jones, P. Identification of Novel, Selective, and Stable Inhibitors of Class II Histone Deacetylases. Validation Studies of the Inhibition of the Enzymatic Activity of HDAC4 by Small Molecules as a Novel Approach for Cancer Therapy. *J. Med. Chem.*, 2009, 52, 6782-6789. (d) Smil, D. V.; Manku, S.; Chanigny, Y. A.; Leit, S.; Wahhab, A.; Yan, T. P.; Fournel, M.; Maroun, C.; Li, Z.; Lemieux, A. M.; Nicolescu, A.; Rahil, J.; Lefebvre, S.; Panetta, A.; Besterman, J. M.; Déziel, R. Novel HDAC6 isoform selective chiral small molecole histone deacetylase inhibitors. *Bioorg. Med. Chem. Lett.* 2009, 19, 688-692. (e) Schäfer, S.; Saunders, L.; Eliseeva, E.; Velena, A.; Jung, M.; Schwienhorst, A.; Strasser, A.; Dickmanns, A.; Ficner, R.; Schlimme, S.; Sippl, W.; Verdin, E.; Jung, M. Phenylalanine-containing hydroxamic acids as selective inhibitors of class IIb histone deacetylases (HDACs). *Bioorg. Med. Chem.* 2008, 16, 2011-2033. (f) Olsen, C. A.; Ghadiri, M. R. Discovery of Potent and Selective Histone Deacetylase Inhibitors via Focused Combinatorial Libraries of Cyclic α3β-Tetrapeptides. *J. Med. Chem.*, 2009, 52, 7836-7846. (g) Schäfer, S.; Saunders, L.; Schlimme, S.; Valkov, V.; Wagner, J. M.; Kratz, F.; Sippl, W.; Verdin, E.; Jung, M. Pyridylalanine-Containing Hydroxamic Acids as Selective HDAC6 Inhibitors. *Chem Med Chem* 2009, 4, 283-290. (h) Smil, D. V.; Manku, S.; Chantigny, Y. A.; Leit, S.; Wahhab, A.; Yan, T. P.; Fournel, M.; Maroun, C.; Li, Z. M.; Lemieux, A.M.; Nicolescu, A.; Rahil, J.; Lefebvre, S.; Panetta, A.; Besterman, J. M.; Deziel, R. Novel HDAC6 isoform selective chiral small molecule histone deacetylase inhibitors. *Bioorg. Med. Chem. Lett.* 2009, 19, 688-692. (i) Gupta, P. K.; Reid, R. C.; Liu, L. G.; Lucke, A. J.; Broomfield, S. A.; Andrews, M. R.; Sweet, M. J.; Fairlie, D. P. Inhibitors selective for HDAC6 in enzymes and cells. *Bioorg. Med. Chem. Lett.* 2010, 20, 7067-7070.

[8]Rivieccio, M. A.; Brochier, C.; Willis, D. E.; Walker, B. A.; D'Annibale, M. A.; McLaughlin, K.; Siddiq, A.; Kozikowski, A. P.; Jaffrey, S. R.; Twiss, J. L.; Ratan, R. R.; Langley, B. HDAC6 is a target for protection and regeneration following injury in the nervous system. *Proc. Natl. Acad. Sci. USA* 2009, 106, 19599-19604.

[9]Wong, J. C.; Hong, R.; Schreiber, S. L. Structural Biasing Elements for In-Cell Histone Deacetylase Paralog Selectivity. *J. Am. Chem. Soc.* 2003, 125, 5586-5587.

[10]Butler, K. V.; Kalin, J.; Brochier, C.; Vistoli, G.; Langley, B.; Kozikowski, A. P. Rational Design and Simple Chemistry Yield a Superior, Neuroprotective HDAC6 Inhibitor, Tubastatin A. *J. Am. Chem. Soc.* 2010, 132, 10842-10846.

[11]Kalin, J. H.; Butler, K. V.; Akimova, T.; Hancock, W. W.; Kozikowski, A. P. Second-generation histone deacetylase 6 inhibitors enhance the immunosuppressive effects of Foxp3+ T-regulatory cells. *J. Med. Chem.* 2012, 55, 639-651.

[12]F. F. Wagner, D. E. Olson, J. P. Gale, T. Kaya, M. Weiwer, N. Aidoud, M. Thomas, E. L. Davoine, B. C. Lemercier, Y. L. Zhang and E. B. Holson, *J Med Chem* 2013, 56, 1772-1776.

[13]a) K. V. Butler, J. Kalin, C. Brochier, G. Vistoli, B. Langley and A. P. Kozikowski, *J Am Chem Soc* 2010, 132, 10842-10846; b) R. De Vreese, T. Verhaeghe, T. Desmet and M. D'Hooghe, *Chem Commun (Camb)* 2013, 49, 3775-3777; c) J. H. Lee, A. Mahendran, Y. Yao, L. Ngo, G. Venta-Perez, M. L. Choy, N. Kim, W. S. Ham, R. Breslow and P. A. Marks, *Proc Natl Acad Sci USA* 2013, 110, 15704-15709; d) C. Blackburn, C. Barrett, J. Chin, K. Garcia, K. Gigstad, A. Gould, J. Gutierrez, S. Harrison, K. Hoar, C. Lynch, R. S. Rowland, C. Tsu, J. Ringeling and H. Xu, *J Med Chem* 2013, 56, 7201-7211; e) C. W. Yu, P. T. Chang, L. W. Hsin and J. W. Chern, *J Med Chem* 2013, 56, 6775-6791; f) D. V. Smil, S. Manku, Y. A. Chantigny, S. Leit, A. Wahhab, T. P. Yan, M. Fournel, C. Maroun, Z. Li, A. M. Lemieux, A. Nicolescu, J. Rahil, S. Lefebvre, A. Panetta, J. M. Besterman and R. Deziel, *Bioorg Med Chem Lett* 2009, 19, 688-692

[14]S. Valente, M. Tardugno, M. Conte, R. Cirilli, A. Perrone, R. Ragno, S. Simeoni, A. Tramontano, S. Massa, A. Nebbioso, M. Miceli, G. Franci, G. Brosch, L. Altucci and A. Mai, *Chem Med Chem* 2011, 6, 698-712

[15]F. Liger, S. Pellet-Rostaing, F. Popowycz and M. Lemaire, *Tetrahedron Letters* 2011, 52, 3736-3739.

[16]Krieger, E.; Koraimann, G.; Vriend, G. Increasing the precision of comparative models with YASARA NOVA—a self-parameterizing force field. *Proteins* 2002, 47, 393-402

[17]Vriend, G. WHAT IF: A molecular modeling and drug design program. *J. Mol. Graph.* 1990, 8, 52-56

[18]Duan, Y.; Wu, C.; Chowdhury, S.; Lee, M. C.; Xiong, G. M.; Zhang, W.; Yang, R.; Cieplak, P.; Luo, R.; Lee, T.; Caldwell, J.; Wang, J. M.; Kollman, P. A point-charge force field for molecular mechanics simulations of proteins based on condensed-phase quantum mechanical calculations. *J. Comput. Chem.* 2003, 24, 1999-2012.

[19]Morris, G. M.; Goodsell, D. S.; Halliday, R. S.; Huey, R.; Hart, W. E.; Belew, R. K.; Olson, A. J. Automated docking using a Lamarckian genetic algorithm and an empirical binding free energy function. *J. Comput. Chem.* 1998, 19, 1639-1662.

[20]Schrodinger, L. L. C. The PyMOL Molecular Graphics System, Version 1.3r1. 2010

[21]J. J. Kovacs, P. J. Murphy, S. Gaillard, X. Zhao, J. T. Wu, C. V. Nicchitta, M. Yoshida, D. O. Toft, W. B. Pratt and T. P. Yao, *Mol Cell* 2005, 18, 601-607.

[22]K. De Bosscher, W. Vanden Berghe, I. M. Beck, W. Van Molle, N. Hennuyer, J. Hapgood, C. Libert, B. Staels, A. Louw and G. Haegeman, *Proc Natl Acad Sci USA* 2005, 102, 15827-15832.

[23]S. Vishwakarma, L. R. Iyer, M. Muley, P. K. Singh, A. Shastry, A. Saxena, J. Kulathingal, G. Vijaykanth, J. Raghul, N. Rajesh, S. Rathinasamy, V. Kachhadia, N. Kilambi, S. Rajgopal, G. Balasubramanian and S. Narayanan, *Int Immunopharmacol* 2013, 16, 72-78.

[24]W. Vanden Berghe, L. Vermeulen, G. De Wilde, K. De Bosscher, E. Boone and G. Haegeman, *Biochemical Pharmacology* 2000, 60, 1185-1195.

[25]S. Plaisance, W. Vanden Berghe, E. Boone, W. Fiers and G. Haegeman, *Mol. Cell. Biol.* 1997, 17, 3733-3743.

The invention claimed is:

1. A compound of formula I, or a stereoisomer, tautomer, racemic, salt, hydrate or solvate thereof

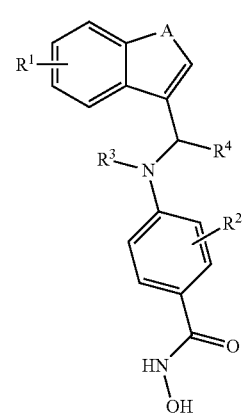

wherein

A is selected from NR, O and S;

R is selected from the group consisting of hydrogen, $C_{1-6}$alkyl, $C_{1-6}$alkenyl, $C_{1-6}$alkynyl, $C_{1-6}$haloalkyl, cycloalkyl, benzyl, and aryl;

$R^1$ is selected from the group consisting of hydrogen, halogen, $C_{1-6}$alkyl, $C_{1-6}$alkenyl, $C_{1-6}$alkynyl, $C_{1-6}$haloalkyl, amino, nitro, hydroxyl, cyano, cycloalkyl, aryl, heterocyclyl, heteroaryl, OR', SR', NR'R", and P(O)(OR')(OR");

R' and R" are independently selected from the group consisting of hydrogen, $C_{1-6}$alkyl, and aryl;

$R^2$ is selected from the group consisting of hydrogen, halogen, $C_{1-6}$alkyl, $C_{1-6}$alkenyl, $C_{1-6}$alkynyl, $C_{1-6}$haloalkyl, amino, nitro, cycloalkyl, aryl, heterocyclyl, and heteroaryl;

$R^3$ is selected from hydrogen, $C_{1-6}$alkyl, cycloalkyl, aryl, heterocyclyl, and heteroaryl;
wherein said $C_{1-6}$alkyl is optionally substituted with halogen, amino, nitro, cycloalkyl, aryl, heterocyclyl, or heteroaryl; and $R^4$ is selected from the group consisting of hydrogen, $C_{1-6}$alkyl, $C_{1-6}$alkenyl, $C_{1-6}$alkynyl, $C_{1-6}$haloalkyl, cycloalkyl, aryl, heterocyclyl, and heteroaryl.

2. The compound of claim 1, wherein A is S.

3. The compound of claim 1, wherein $R^1$ is selected from the group consisting of hydrogen, halogen, $C_{1-6}$alkyl, $C_{1-6}$alkenyl, $C_{1-6}$alkynyl, $C_{1-6}$haloalkyl, amino, nitro, cycloalkyl, aryl, heterocyclyl, and heteroaryl.

4. The compound of claim 3, wherein $R^1$ is selected from hydrogen, halogen, and aryl.

5. The compound of claim 1, wherein $R^2$ is selected from the group consisting of hydrogen, halogen, $C_{1-6}$alkyl, amino, and nitro.

6. The compound of claim 5, wherein $R^2$ is hydrogen or methyl.

7. The compound of claim 1, wherein $R^3$ is selected from hydrogen or $C_{1-6}$alkyl optionally substituted with halogen, amino, nitro, cycloalkyl, aryl, heterocyclyl, or heteroaryl.

8. The compound of claim 7, wherein $R^3$ is selected from hydrogen and $C_{1-6}$alkyl substituted with phenyl.

9. The compound of claim 1, wherein $R^1$ is hydrogen or halogen; and $R^2$ is hydrogen.

10. The compound of claim 1, selected from the group consisting of:

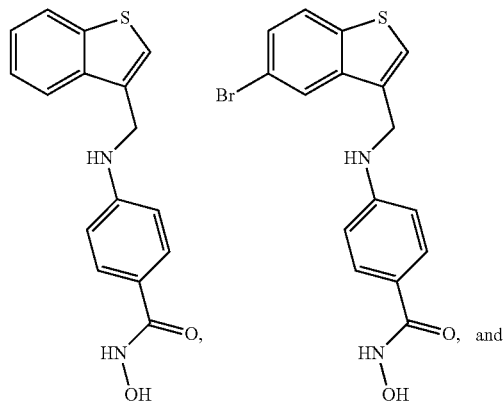

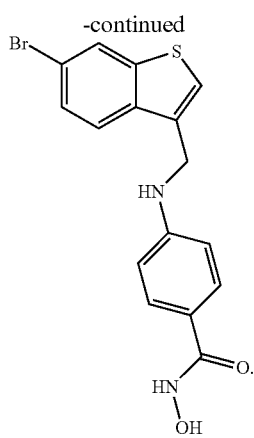

11. A composition comprising a compound according to claim 1, and one or more pharmaceutically acceptable carriers, diluents, and/or excipients.

12. The composition of claim 11, wherein the composition is in a form suitable for oral administration, parenteral administration, topical administration, administration by inhalation, administration by a skin patch, administration by an implant, or administration by a suppository.

13. A method for inhibiting histone deacetylase (HDAC) in a subject in need thereof, said method comprising administering an effective amount of the compound according to claim 1 to the subject.

14. The method according to claim 13, wherein the subject has an HDAC-associated disease selected from the group consisting of a cell proliferative disease, an autoimmune disease, an inflammatory disorder, a neurodegenerative disease, a viral disease, malaria, or a combination thereof.

15. The method according to claim 14, wherein the subject has a cell proliferative disease.

16. The method according to claim 15, wherein the cell proliferative disease is cancer or metastasis thereof.

17. A method for treating cancer in a subject in need thereof, the method comprising administering a therapeutically effective amount of a compound according to claim 1 to the subject.

18. A method for treating cancer in a subject in need thereof, the method comprising administering a therapeutically effective amount of a composition according to claim 11 to the subject.

* * * * *